US006355825B1

(12) United States Patent
Piscopio et al.

(10) Patent No.: US 6,355,825 B1
(45) Date of Patent: Mar. 12, 2002

(54) PROCESSES AND INTERMEDIATES FOR PREPARING SUBSTITUTED CHROMANOL DERIVATIVES

(75) Inventors: Anthony Piscopio, Longmount, CO (US); Joel M. Hawkins, Old Lyme, CT (US); Stephanie Caron, Groton, CT (US); Sarah E. Kelly, Mystic, CT (US); Jeffrey W. Raggon, Uncasville, CT (US); Michael J. Castaldi, Pawcatuck, CT (US); Robert W. Dugger, Stonington, CT (US); Sally G. Ruggeri, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/813,546

(22) Filed: Mar. 21, 2001

Related U.S. Application Data

(62) Division of application No. 09/511,475, filed on Feb. 23, 2000, now Pat. No. 6,288,242, which is a division of application No. 09/367,235, filed as application No. PCT/IB97/01024 on Aug. 25, 1997, now Pat. No. 6,096,906.
(60) Provisional application No. 60/026,372, filed on Sep. 16, 1996.

(51) Int. Cl.$^7$ .................................................. C07F 5/04
(52) U.S. Cl. ........................................ 558/289; 558/298
(58) Field of Search ................................ 558/289, 298

(56) References Cited

U.S. PATENT DOCUMENTS 5,356,893 A * 10/1994 Bradshaw et al. ........ 514/227.2

* cited by examiner

Primary Examiner—Bernard Dentz
(74) Attorney, Agent, or Firm—Peter C. Richardson; Paul H. Ginsburg; Jolene W. Appleman

(57) ABSTRACT

The invention relates to processes for preparing a compound of the formula

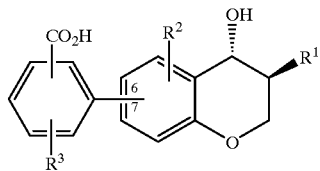

X and the enantiomer of said compound, wherein the benzoic acid moiety is attached at position 6 or 7 of the chroman ring, and $R^1$, $R^2$, and $R^3$ are as defined herein. The invention further relates to intermediates that are useful in the preparation of the compound of formula X above.

3 Claims, No Drawings

PROCESSES AND INTERMEDIATES FOR PREPARING SUBSTITUTED CHROMANOL DERIVATIVES

CROSS REFERENCE TO RELATED APPLICATIONS

This application is a divisional of U.S. application Ser. No. 09/511,475 filed Feb. 23, 2000 now U.S. Pat. No. 6,288,242, which is a divisional of U.S. application Ser. No. 09/367,235 filed Mar. 5, 1999 now U.S. Pat. No. 6,096,906, which is the National Stage of International Application No. PCT/IB97/01024 having an international filing date of Aug. 25, 1997 designating inter alia the United States Provisional Application No. 60/026,372 which has a priority filing date of Sep. 16, 1996.

BACKGROUND OF THE INVENTION

This invention relates to the preparation of substituted chromanol derivatives and to intermediates useful in said preparation. The substituted chromanol derivatives that are prepared in accord with the present invention are disclosed in U.S. patent application Ser. No. 08/295,827, filed Jan. 9, 1995, entitled "Benzopyran And Related $LTB_4$ Antagonists," now U.S. Pat. No. 5,552,435, PCT international application publication number WO 96/11925 (published Apr. 25, 1996), PCT international application publication number WO 96/11920 (published Apr. 25, 1996), PCT international application publication number WO 93/15066 (published Aug. 5,1993). Each of the foregoing United States and PCT internation patent applications are incorporated herein by reference in their entirety.

The substituted chromanol derivatives that are prepared in accord with the present invention inhibit the action of $LTB_4$, as disclosed in U.S. patent application Ser. No. 08/295,827, referred to above. As $LTB_4$ antagonists, the substituted chromanol derivatives that are prepared according to the present invention are useful in the treatment of $LTB_4$-induced illnesses such as inflammatory disorders including rheumatoid arthritis, osteoarthritis, inflammatory bowel disease, psoriasis, eczema, erythma, pruritis, acne, stroke, graft rejection, autoimmune diseases, and asthma.

SUMMARY OF THE INVENTION

The present invention relates to a process of preparing a compound of the formula

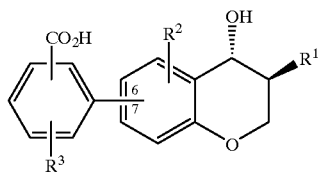

X or the enantiomer of said compound, wherein in said compound of formula X the $R^3$-substituted benzoic acid moiety is attached at carbon 6 or 7 of the chroman ring;

$R^1$ is $-(CH_2)_qCHR^5R^6$ wherein q is 0 to 4;

each $R^2$ and $R^3$ is independently selected from the group consisting of H, fluoro, chloro, $C_1-C_6$ alkyl, $C_1-C_6$ alkoxy, phenylsulfinyl, phenylsulfonyl, and $-S(O)_n$ ($C_1-C_6$ alkyl) wherein n is 0 to 2, and wherein said alkyl group, the alkyl moiety of said alkoxy and $-S(O)_n$ ($C_1-C_6$ alkyl) groups, and the phenyl moiety of said phenylsulfinyl and phenylsulfonyl groups are optionally substituted by 1 to 3 fluoro groups;

$R^5$ is H, $C_1-C_6$ alkyl, or phenyl substituted by $R^2$;

$R^6$ is H, $C_1-C_6$ alkyl, $C_3-C_8$ cycloalkyl, $C_6-C_{10}$ aryl, or 5–10 membered heteroaryl, wherein said aryl and heteroaryl groups are optionally substituted by 1 or 2 substituents independently selected from phenyl, $R^2$, and phenyl substituted by 1 or 2 $R^2$;

which comprises treating a compound of the formula

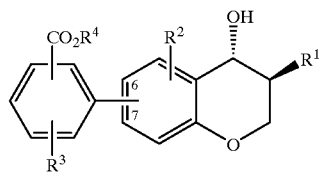

IX or the enantiomer of said compound of formula IX in the preparation of the enantiomer of said compound of formula X, wherein $R^1$, $R^2$, and $R^3$ are as defined above, $R^4$ is $C_1-C_6$ alkyl, and the benzoate moiety is attached to position 6 or 7 of the chroman ring, with a base.

In said process of preparing the compound of formula X, the compound of formula IX is preferably treated with an aqueous hydroxide base, $R^1$ is preferably benzyl, 4-fluorobenzyl, 4-phenylbenzyl, 4-(4-fluorophenyl)benzyl, or phenethyl, $R^2$ is preferably hydrogen or fluoro, $R^3$ is preferably fluoro, chloro, or methyl optionally substituted by 1 to 3 fluorines, and $R^4$ is preferably ethyl or 2,2-dimethylpropyl. Most preferably, said compound of formula IX is treated with a base comprising aqueous sodium hydroxide, said compound of formula IX is (3S,4R)-2-(3-benzyl-4-hydroxy-chroman-7-yl)-4-trifluoromet hyl-benzoic acid ethyl ester, and said compound of formula X is (3S,4R)-2-(3-benzyl-4-hydroxy-chroman-7-yl)-4-trifluoromethyl-benzoicacid.

In a further aspect of the present invention, said compound of formula IX, or the enantiomer of said compound, wherein $R^1$, $R^2$, $R^3$, and $R^4$ are as defined above, is prepared by treating a compound of the formula

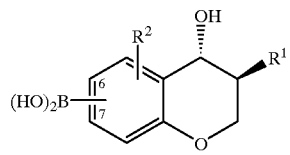

VII or the enantiomer of said compound of formula VII in the preparation of the enantiomer of the compound of formula IX, wherein $R^1$ and $R^2$ are as defined above and the boronic acid moiety is attached at position 6 or 7 of the chroman ring, with a compound of the formula

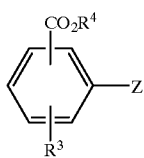

VIII wherein $R^3$ and $R^4$ are as defined above and Z is halo or $C_1$–$C_4$ perfluoroalkylsulfonate, in the presence of a base or fluoride salt and a palladium catalyst.

In said process of making the compound of formula IX, or the enantiomer of said compound, preferred substituents for $R^1$, $R^2$, $R^3$ and $R^4$ are as stated above for said process of making the compound of formula X. In another preferred embodiment, Z is halo, the base or fluoride salt is selected from sodium carbonate, triethylamine, sodium bicarbonate, cesium carbonate, tripotassium phosphate, potassium fluoride, cesium fluoride, sodium hydroxide, barium hydroxide, and tetrabutylammonium fluoride, the palladium catalyst is selected from tetrakis(triphenylphosphine)palladium(0), dichlorobis(triphenylphosphine)palladium (II), palladium(II) acetate, allylpalladium chloride dimer, tris(dibenzylideneacetone)dipalladium(0), and 10% palladium on carbon. Most preferably, the base or fluoride salt is potassium fluoride, the palladium catalyst is 10% palladium on carbon, the compound of formula VII is (3$\underline{S}$,4$\underline{R}$)-(3-benzyl-4-hydroxy-chroman-7-yl)-boronic acid, and the compound of formula VIII is ethyl 2-iodo-4-trifluoromethyl-benzoate.

In a further aspect of the invention, the compound of formula VII, or the enantiomer of said compound, wherein $R^1$ and $R^2$ are as defined above, is prepared by treating a compound of the formula

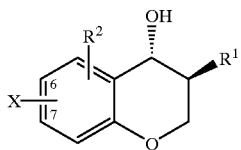

VI or the enantiomer of said compound of formula VI in the preparation of the enantiomer of the compound of formula VII, wherein $R^1$ and $R^2$ are as defined above and X is a halide and is attached at position 6 or 7 of the chroman ring, with (1) $C_1$–$C_4$ alkyl lithium, and (2) a borating agent.

In said process of making the compound of formula VII, or the enantiomer of said compound, preferred substituents for $R^1$ and $R^2$ are as stated above for said process of making the compound of formula X. In another preferred embodiment, X is bromo or iodo, and said compound of formula VI is treated with (1) methyl lithium, (2) butyl lithium, and (3) said borating agent which is selected from borane-tetrahydrofuran complex, triisopropyl borate, and trimethyl borate. Most preferably, the compound of formula VI is (3$\underline{S}$,4$\underline{R}$)-3-benzyl-7-bromo-chroman-4-ol and said borating agent is borane-tetrahydrofuran complex.

In a further aspect of the invention, the compound of formula VI, or the enantiomer of said compound, wherein $R^1$, $R^2$ and X are as defined above, is prepared by treating a compound of the formula

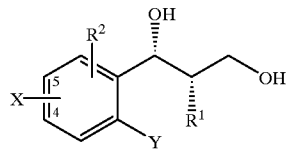

V or the enantiomer of said compound of formula V in the preparation of the enantiomer of the compound of formula VI, wherein $R^1$, $R^2$ and X are as defined above and X is attached at position 4 or 5 of the phenyl ring, and Y is halo or nitro, with a base, optionally in the presence of added copper salts.

In said process of making the compound of formula VI, or the enantiomer of said compound, preferred substituents for $R^1$, $R^2$ and X are as stated above for said process of making the compound of formula VII. In another preferred embodiment, Y is halo, and said base is potassium tert-butoxide, sodium bis(trimethylsilyl)amide, potassium bis(trimethylsilyl)amide, cesium carbonate, or sodium hydride. Most preferably, said base is potassium tert-butoxide and the compound of formula V is (1$\underline{S}$,2$\underline{R}$)-2-benzyl-1-(4-bromo-2-fluoro-phenyl)-propane-1,3-diol.

In a further aspect of the invention, the compound of formula V, or the enantiomer of said compound, wherein $R^1$, $R^2$, X and Y are as defined above, is prepared by treating a compound of the formula

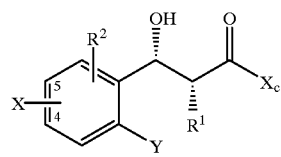

IV or the enantiomer of said compound of formula IV in the preparation of the enantiomer of the compound of formula V, wherein $R^1$, $R^2$, X and Y are as defined above and X is attached at position 4 or 5 of the phenyl ring, and $X_c$ is a chiral auxiliary, with a hydride reducing agent.

In said process of making the compound of formula V, or the enantiomer of said compound, preferred substituents for $R^1$, $R^2$, X and Y are as stated above for said process of making the compound of formula VI. In another preferred embodiment, $X_c$ is ($\underline{R}$)-4-benzyl-2-oxazolidinone, ($\underline{S}$)-4-benzyl-2-oxazolidinone, (3$\underline{S}$,4$\underline{R}$)-4-methyl-5-phenyl-oxazolidin-2-one, or (3$\underline{S}$,4$\underline{R}$)-4-methyl-5-phenyl-oxazolidin-2-one, wherein said $X_c$ is attached at the nitrogen of the oxazolidin-2-one ring, and said reducing agent is lithium borohydride, lithium aluminum hydride, sodium borohydride, or calcium borohydride. Most preferably, the compound of formula IV is [4$\underline{R}$-[3(2$\underline{R}$,3$\underline{R}$)]]-4-benzyl-3-[2-benzyl-3-(4-bromo-2-fluoro-phenyl)-3-hydroxy-propionyl]-oxazolidin-2-one, 1-methyl-2-pyrrolidinone solvate or [4$\underline{R}$-[3(2$\underline{R}$,3$\underline{R}$)]]-4-benzyl-3-[2-benzyl-3-(4-bromo-2-fluoro-phenyl)-3-hydroxy-propionyl]-oxazolidin-2-one, and said reducing agent is lithium borohydride.

In a further aspect of the invention, the compound of formula IV, or the enantiomer of said compound, wherein $R^1$, $R^2$, X, $X_c$ and Y are as defined above, is prepared by treating a compound of the formula $R^1$—$CH_2C(O)$—$X_c$, wherein $R^1$ and $X_c$ are as defined above, with (1) a Lewis acid, (2) a base, and (3) a compound of formula

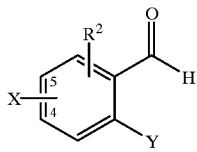

III wherein $R^2$, X and Y are as defined above and X is attached at position 4 or 5 of the phenyl ring.

In said process of making the compound of formula IV, or the enantiomer of said compound, preferred substituents for $R^1$, $R^2$, X, $X_c$ and Y are as stated above for said process of making the compound of formula V. In another preferred embodiment, said Lewis acid is a boron halide or sulfonate, and said base is triethylamine or diisopropylethylamine. Most preferably, said compound of formula $R^1$—$CH_2C$(O)—$X_c$ is (R)-4-benzyl-3-(3-phenyl-propionyl)-oxazolidin-2-one, said compound of formula III is 4-bromo-2-fluoro-benzaldehyde, said Lewis acid is dibutylboron triflate, and said base is triethylamine.

In a further aspect of the invention, the compound of formula IV, or the enantiomer of said compound, wherein $R^1$, $R^2$, X, $X_c$ and Y are as defined above, is prepared by treating a compound of the formula $R^1$—$CH_2C(O)$—$X_c$, wherein $R^1$ and $X_c$ are as defined above, with (1) a titanium (IV) halide, (2) a base optionally followed by treatment with a donor ligand, and (3) a compound of formula

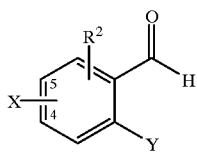

III wherein $R^2$, X and Y are as defined above and X is attached at position 4 or 5 of the phenyl ring.

In said process of making the compound of formula IV, or the enantiomer of said compound, preferred substituents for $R^1$, $R^2$, X, $X_c$ and Y are as stated above for said process of making the compound of formula V. In another preferred embodiment, said titanium(IV) halide is titanium tetrachloride, and said base is a tertiary amine or tertiary diamine base. In another preferred embodiment, said base is triethylamine or N,N,N',N'-tetramethylethylenediamine, and said treatment with said base is followed by treatment with a donor ligand selected from 1-methyl-2-pyrrolidinone, dimethylformamide, 1,3-dimethyl-3,4,5,6-tetrahydro-2(1H)-pyrimidinone, triethylphosphate, and 2,2'-dipyridyl. Most preferably, said compound of formula $R^1$—$CH_2C$(O)—$X_c$ is (R)-4-benzyl-3-(3-phenyl-propionyl)-oxazolidin-2-one, said compound of formula III is 4-bromo-2-fluoro-benzaldehyde, said base is N,N,N',N'-tetramethylethylenediamine, and said donor ligand is 1-methyl-2-pyrrolidinone.

In a further aspect of the invention, said compound of formula IX, or the enantiomer of said compound, wherein $R^1$, $R^2$, $R^3$ and $R^4$ are as defined above, is prepared by coupling a compound of the formula

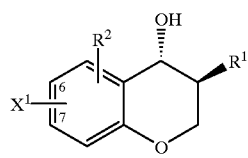

VI or the enantiomer of said compound in the preparation of the enantiomer of the compound of formula IX, wherein $R^1$ and $R^2$ are as defined above and X', which is attached at position 6 or 7 of the chroman ring, is halo or $C_1$–$C_4$ perfluoroalkylsulfonate, with a compound of the formula

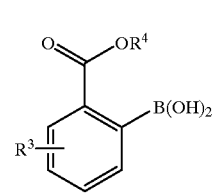

XIV wherein $R^3$ and $R^4$ are as defined above, in the presence of a base or fluoride salt and a palladium catalyst.

In the process of preparing the compound of formula IX, or the enantiomer of said compound, as recited directly above, preferred substituents for $R^1$, $R^2$, $R^3$ and $R^4$ are as stated above for the process of making the compound of formula X. In another preferred embodiment, X' is preferably bromo, iodo, or trifluoromethanesulfonate, the palladium catalyst is preferably selected from tetrakis(triphenylphosphine)palladium(0), dichlorobis(triphenylphosphine)palladium(II), palladium(II) acetate, allylpalladium chloride dimer, tris(dibenzylideneacetone)dipalladium(0), and 10% palladium on carbon, and the base or fluoride salt is selected from sodium carbonate, triethylamine, sodium bicarbonate, cesium carbonate, tripotassium phosphate, potassium fluoride, cesium fluoride, sodium hydroxide, barium hydroxide, and tetrabutylammonium fluoride. Most preferably, the compound of formula VI is (3S,4R)-3-benzyl-7-bromo-chroman-4-ol, the compound of formula XIV is 2-(2,2-dimethyl-propoxycarbonyl-5-trifluoromethyl-benzeneboronic acid, the base or fluoride salt is sodium carbonate, and the palladium catalyst is tetrakis(triphenylphosphine)palladium(0).

In a further aspect of the invention, the compound of formula XIV, wherein $R^3$ and $R^4$ are as defined above, is prepared by hydrolyzing a compound of the formula

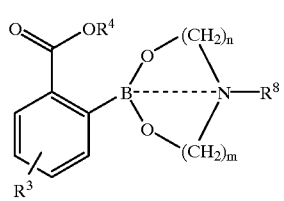

XVI wherein $R^3$ and $R^4$ are as define above, the dashed line indicates a bond or no bond between the B and N atoms, n and m are independently 2 to 5, and $R^8$ is H or $C_1$–$C_6$ alkyl. $R^8$ is preferably H and preferred substituents for $R^3$ and $R^4$ are as stated above for said process of making a compound of formula X. Preferably, said hydrolysis is effected with an acid, such as hydrochloric acid, and n and m are each 2. Most preferably, said compound of formula XVI is 2-[1,3,6,2]dioxazaborocan-2-yl-4-trifluoromethyl-benzoic acid 2,2-dimethyl-propyl ester.

In a further aspect of the invention, the compound of formula XVI, wherein $R^3$, $R^4$ and $R^8$ are as defined above, is prepared by reacting a compound of formula XIV, wherein $R^3$ and $R^4$ are as defined above, with a compound of formula $HO(CH_2)_m-N(R^8)-(CH_2)_nOH$ (formula XV), wherein n, m and $R^8$ are as defined above. In said process of preparing the compound of formula XVI, preferred substituents for $R^3$ and $R^4$ are as stated above for said process of preparing a compound of formula X. Most preferably, said compound of formula XIV is 2-(2,2-dimethyl-propoxycarbonyl)-5-trifluoromethyl-benzeneboronic acid and said compound of formula XV is diethanolamine.

In a further aspect of the invention, the compound of formula XIV, wherein $R^4$ and $R^3$ are as defined above, is prepared by hydrolyzing a compound of the formula

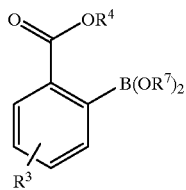

XIII wherein $R^3$ and $R^4$ are as defined above and $R^7$ is $C_1-C_6$ alkyl. Said hydrolysis is preferably effected with an acid, such as hydrochloric acid. Preferred substituents for $R^3$ and $R^4$ are as stated above for said process of making a compound of formula X.

In a further aspect of the invention, the compound of formula XVI, wherein $R^3$, $R^4$ and $R^7$ are as defined above, is prepared by treating a compound of the formula

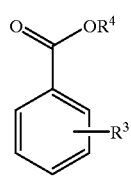

XII wherein $R^3$ and $R^4$ are as defined above, with a metal amide base in the presence of a tri-($C_1-C_6$ alkyl)borate.

In said process of making the compound of formula XIII, preferred substituents for $R^3$ and $R^4$ are as stated above for said process of making the compound of formula X. In another preferred embodiment, said metal amide base is selected from lithium diisopropylamide, lithium diethylamide, lithium 2,2,6,6-tetramethylpiperidine, and bis(2,2,6,6-tetramethylpiperidino)magnesium, and said tri-($C_1-C_4$alkyl)borate is selected from triisopropylborate, triethylborate, and trimethylborate. Most preferably, the compound of formula XII is 4-trifluoromethyl-benzoic acid 2,2-dimethyl-propyl ester, said metal amide base is lithium diisopropylamide, and said tri-($C_1-C_6$ alkyl)borate is triisopropylborate.

In a further aspect of the invention, the compound of formula X, or the enantiomer of said compound, wherein $R^1$, $R^2$, and $R^3$ are as defined above, is reacted with a secondary amine of the formula $NHR^5R^6$, wherein $R^5$ and $R^6$ are as defined above, to form an ammonium carboxylate of the formula

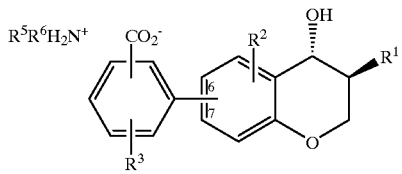

XVII or the enantiomer of said compound of formula XVII, wherein $R^1$, $R^2$, $R^3$, $R^5$ and $R^6$ are as defined above. Preferred substituents for $R^1$, $R^2$, and $R^3$ are as stated above for said process of making a compound of formula X. In said secondary amine, $R^5$ and $R^6$ are each preferably cyclohexyl. Most preferably, said compound of formula XVII is (3$\underline{S}$,4$\underline{R}$)-dicyclo hexylammonium-2-(3-benzyl-4-hydroxy-chroman-7-yl)-4-trifluoromethyl benzoate.

The invention also relates to a process of preparing a compound of the formula

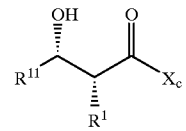

XIX or the enantiomer of said compound, wherein $R^1$ and $X_c$ are as defined above for said process of preparing a compound of formula V, and $R^{11}$ is $C_1-C_9$ alkyl, $C_2-C_9$ alkenyl or phenyl substituted by Y in the 2 position, X in the 4 or 5 position, and $R^2$ in one of the remaining positions of the phenyl moiety, wherein Y, X and $R^2$ are as defined above for said process of preparing a compound of formula V, by treating a compound of the formula $R^1-CH_2C(O)-X_c$, wherein $R^1$ and $X_c$ are as defined above, with (1) a titanium(IV) halide, (2) a base optionally followed by treatment with a donor ligand, and (3) less than 2 equivalents, preferably about 1 equivalent, of a compound of the formula $R^{11}-C(O)H$, wherein $R^{11}$ is as defined above, relative to the amount of said compound of formula $R^1-CH_2C(O)-X_c$. Preferred substituents and reagents for said process of preparing said compound of formula XIX, or the enantiomer of said compound, are as stated above for said process of preparing a compound of formula IV using said titanium(IV) halide.

The invention also relates to a compound of the formula

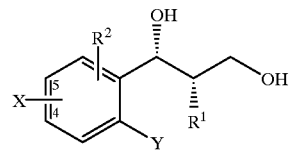

V and to the enantiomer of said compound, wherein $R^1$, $R^2$, X and Y are as stated above for said process of preparing a compound of the formula VI.

In said compound of formula V, and the enantiomer of said compound, preferred substituents for $R^1$, $R^2$, X and Y are as stated above for said process of preparing a compound of the formula VI. Most preferably, said compound of formula V is (1<u>R</u>,2<u>S</u>)-2-benzyl-1-(4-bromo-2-fluoro-phenyl)-propane-1,3-diol.

The invention also relates to a compound of the formula

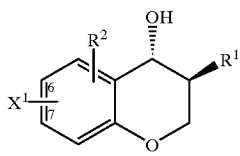

VI and to the enantiomer of said compound, wherein $R^1$ and $R^2$ are as stated above for said compound of formula V and X' is halo or $C_1$–$C_4$ perfluoroalkylsulfonate and is attached at position 6 or 7 of the chroman ring.

In said compound of formula VI, and the enantiomer of said compound, preferred substituents for $R^1$ and $R^2$ are as stated above for said compound of formula V, and X' is preferably bromo, iodo, or trifluoromethanesulfonate. Most preferably, said compound of the formula VI is (3<u>S</u>,4<u>R</u>)-3-benzyl-7-bromo-chroman-4-ol.

The invention also relates to a compound of the formula

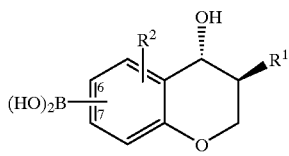

VII and to the enantiomer of said compound, wherein $R^1$ and $R^2$ are as stated above for said compound of formula VI.

In said compound of formula VII, and the enantiomer of said compound, preferred substituents for $R^1$ and $R^2$ are as stated above for said compound of formula VI. Most preferably, said compound of the formula VII is (3<u>S</u>,4<u>R</u>)-(3-benzyl-4-hydroxy-chroman-7-yl)-boronic acid.

The invention also relates to a compound of the formula

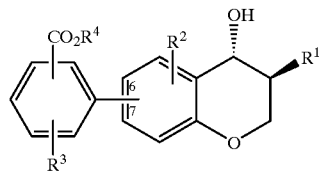

IX and to the enantiomer of said compound, wherein $R^1$, $R^2$, $R^3$ and $R^4$ are as stated above for said process of preparing a compound of the formula X and the benzoate moiety is attached to position 6 or 7 of the chroman ring.

In said compound of formula IX, and the enantiomer of said compound, preferred substituents for $R^1$, $R^2$, $R^3$ and $R^4$ are as stated above for said process of preparing a compound of the formula X. Most preferably, the compound of formula IX is (3<u>S</u>,4<u>R</u>)-2-(3-benzyl-4-hydroxy-chroman-7-yl)-4-trifluoromethyl-benzoacide ethylester.

The invention also relates to a compound of the formula

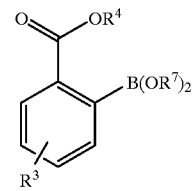

XIII wherein $R^3$, $R^4$ and $R^7$ are as stated above for said process of preparing a compound of the formula XIV using a compound of formula XIII.

In said compound of formula XII, preferred substituents for $R^7$, $R^3$ and $R^4$ are as stated above for said process of preparing a compound of the formula XIV using a compound of formula XIII.

The invention also relates to a compound of the formula

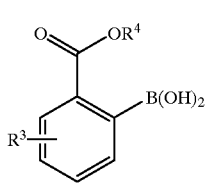

XIV wherein $R^3$ and $R^4$ are as stated above for said compound of formula XIII.

In said compound of formula XIV, preferred substituents for $R^3$ and $R^4$ are as stated above for said compound of formula XII. Most preferably, said compound of the formula XIV is 2-(2,2-dimethyl-propoxycarbonyl)-5-trifluoromethyl-benzeneboronic acid.

The invention also relates to compounds of the formula

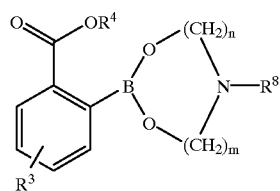

XVI wherein the dashed line indicates a bond or no bond between the B and N atoms, n and m are independently 2 to 5, $R^3$ and $R^4$ are as defined above for said compound of formula XIV, and $R^8$ is H or $C_1$–$C_6$ alkyl.

In said compound of formula XVI, n and m are each preferably 2, preferred substituents for $R^3$ and $R^4$ are as defined above for said compound of formula XIV, and $R^8$ is preferably H. Most preferably, the compound of formula XVI is 2-[1,3,6,2]dioxazaborocan-2-yl-4-trifluoromethyl-benzoicacid 2,2-dimethyl-propyl ester.

The invention also relates to an ammonium carboxylate compound of the formula

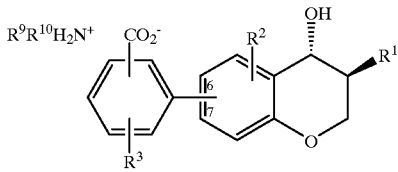

XVII

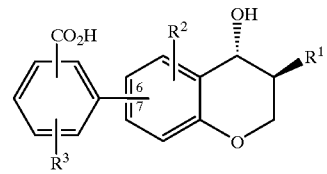

X and to the enantiomer of said compound, wherein $R^1$, $R^2$, $R^3$, $R^5$ and $R^6$ are as defined above for said process of preparing a compound of the formula X. Preferred substituents for $R^1$, $R^2$, and $R^3$ are as stated above for said process of making a compound of formula X. In the ammonium moiety, $R^5$ and $R^6$ are each preferably cyclohexyl. Most preferably, said compound of formula XVII is (3S,4R)-dicyclohexylammonium-2-(3-benzyl-4-hydroxy-chroman-7-yl)-4-trifluoromethyl benzoate.

The present invention also relates to a compound of the formula

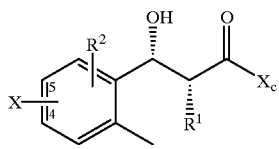

IV and to the enantiomer of said compound, wherein $R^1$, $R^2$, X, Y and $X_c$ are as defined above for said process of preparing a compound of formula V. The present invention also relates to solvates of said compound of formula IV and the enantiomer of said compound of formula IV. Preferred solvates of said compound of formula IV, and the enantiomer of said compound, are those formed with a donor ligand selected from 1-methyl-2-pyrrolidinone, dimethylformamide, 1,3-dimethyl-3,4,5,6-tetrahydro-2(1H)-pyrimidinone, triethylphosphate, and 2,2'-dipyridyl. The preferred compound of formula IV is [4R-[3(2R,3R)]]-4-benzyl-3-[2-benzyl-3-(4-bromo-2-fluoro-phenyl)-3-hydroxy-propionyl]-oxazolidin-2-one, and the preferred solvate of said compound is [4R-[3(2R,3R)]]-4-benzyl-3-[2-benzyl-3-(4-bromo-2-fluoro-phenyl)-3-hydroxy-propionyl]-oxazolidin-2-one, 1-methyl-2-pyrrolidinone solvate.

The term "halo", as used herein, unless otherwise indicated, means fluoro, chloro, bromo or iodo.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived form an aromatic hydrocarbon by removal of one hydrogen, such as phenyl or naphthyl.

The term "heteroaryl", as used herein, unless otherwise indicated, includes an organic radical derived from an aromatic heterocyclic compound by removal of one hydrogen, such as pyridyl, furyl, thienyl, isoquinolyl, pyrimidinyl, and pyrazinyl.

The term "enantiomer" as used herein in reference to the compound of formula X means a compound of the formula

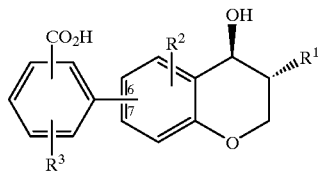

The term "enantiomer" as used herein in reference to the compound of formula IX

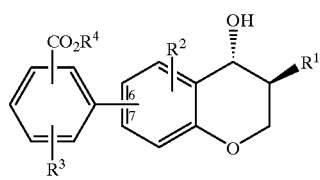

IX means a compound of the formula

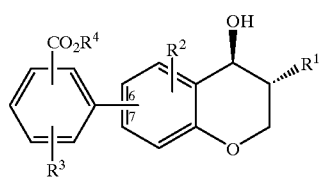

The term "enantiomer" as used herein in reference to a compound of formula VII

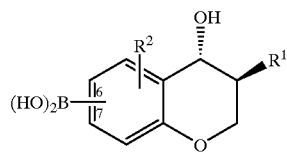

VII means a compound of the formula

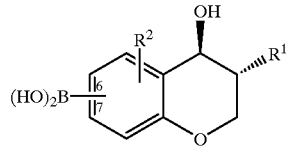

The term "enantiomer" as used herein in reference to a compound of the formula VI

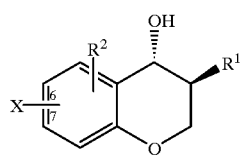

VI means a compound of the formula

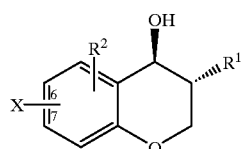

The term "enantiomer" as used herein in reference to a compound of the formula V

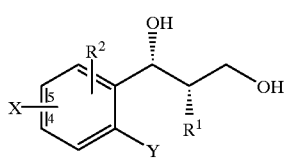

V means a compound of the formula

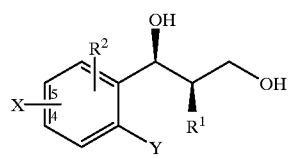

The term "enantiomer" as used herein in reference to a compound of the formula IV

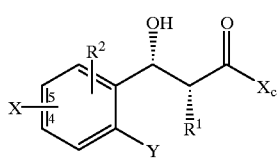

IV means a compound of the formula

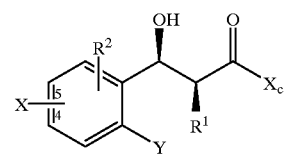

The term "enantiomer" as used herein in reference to a compound of the formula XVII

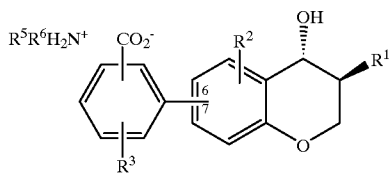

XVII means a compound of the formula

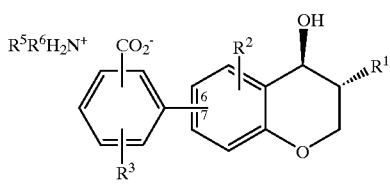

The term "enantiomer" as used herein in reference to a compound of the formula XIX

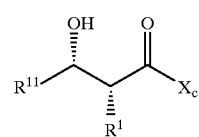

XIX means a compound of the formula

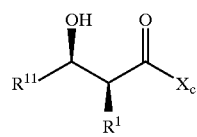

DETAILED DESCRIPTION OF THE INVENTION

The process of the present invention and the preparation of the compounds of the present invention are illustrated in the following Schemes. In the following Schemes and discussion that follows, unless otherwise indicated, $R^1$, $R^2$, $R^3$, $R^4$, $R^5$, $R^6$, $R^7$, $R^8$, $R^{11}$, Y, Z, X, $X_c$, and X' are as defined above. The following Schemes and the discussion that follows describe the preparation of the compounds of formulas I–XIX. The following Schemes and description that follows also applies to the enantiomers of the compounds of formulas I–XIX, wherein the term "enantiomer" is as defined above.

SCHEME 1
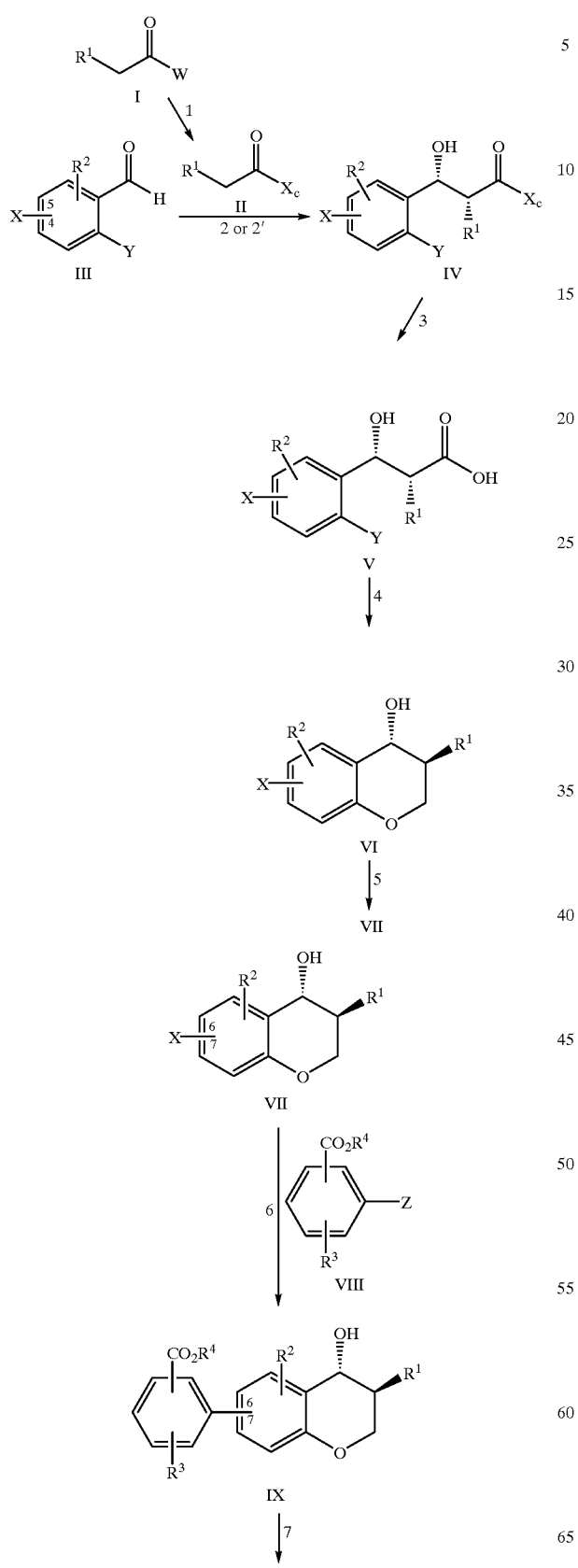
SCHEME 2
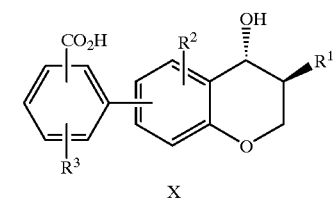
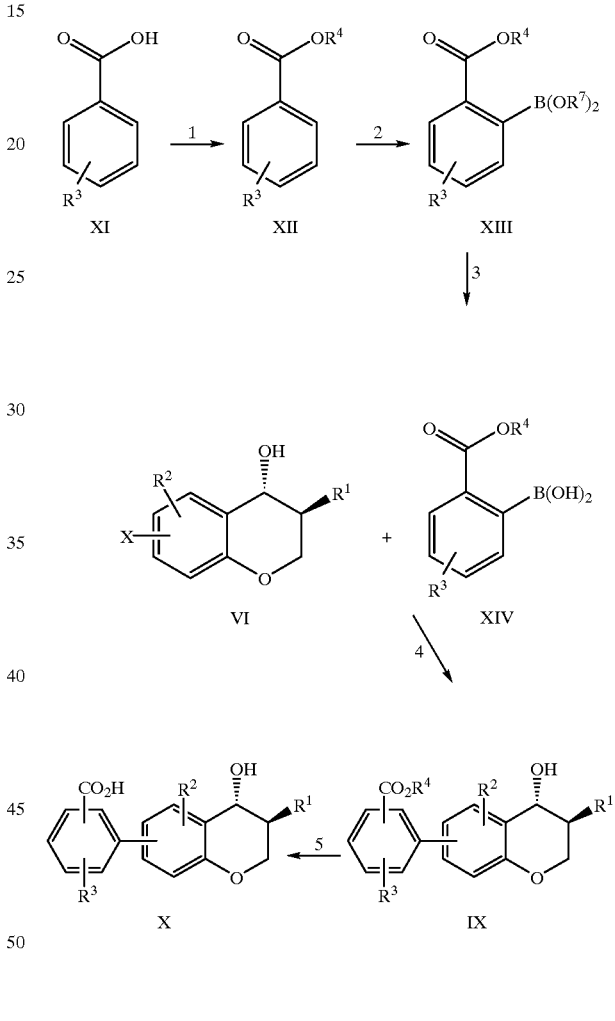
SCHEME 3
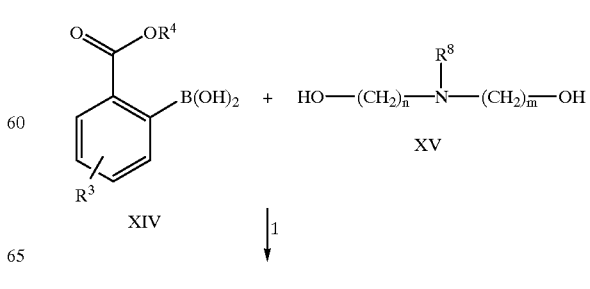

-continued

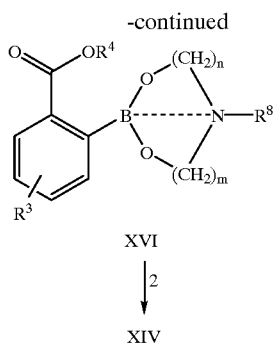

XVI

↓2

XIV

SCHEME 4

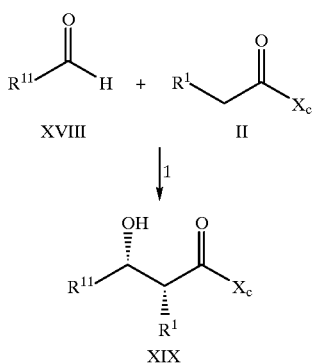

Overall, the synthetic sequence in Scheme I involves attaching chiral auxiliary $X_c$ to $R^1$-containing compound I (step 1), asymmetric aldol condensation with aldehyde III (step 2 or 2'), reductive removal of the chiral auxiliary from aldol IV (step 3), base-mediated cyclization of diol V (step 4), lithiation and boration of halochromanol VI (step 5), coupling boronic acid VII with aryl halide or sulfonate VIII (step 6), and hydrolysis of ester IX (step 7).

In step 1 of Scheme 1, chiral auxiliary $HX_c$ is converted to the corresponding anion by treatment with a suitably strong base, such as an alkyllithium base, preferably butyllithium, in an aprotic solvent, such as an ethereal solvent, preferably tetrahydrofuran (THF), at a temperature of approximately −80 to 0° C., preferably −78 to −55° C., over a period of about 20 minutes to one hour. Substituent $X_c$ is a chiral auxiliary that is suitable to control relative and absolute stereochemistry in asymmetric aldol reactions. Examples of $HX_c$ include (R)-4-benzyl-2-oxazolidinone, (S)-4-benzyl-2-oxazolidinone, (4R,5S)-4-methyl-5-phenyl-oxazolidin-2-one, and (4S,5R)-4-methyl-5-phenyl-oxazolidin-2-one. The resulting anion is treated with acylating agent I, wherein group W is a halide, preferably chloride, and $R^1$ is as defined above, in the same solvent at a temperature of approximately −80 to 0° C., preferably about −75° C., over a period of about one hour, and then warmed to approximately −20 to 20° C., preferably about 0° C., before aqueous workup, which is preferably done by treatment with aqueous sodium bicarbonate, to yield acylated chiral auxiliary II.

Step 2 of Scheme 1 is an "Evans aldol" reaction that is performed under conditions that are analogous to those described in Evans, D. A.; Bartroli, J.; Shih, T. L., J. Am. Chem. Soc. 1981, 103, 2127 and Gage, J. R.; Evans, D. A., Org. Syn. 1989, 68, 83, both of which references are incorporated herein by reference. In particular, in step 2 of Scheme 1, the acylated chiral auxiliary II is treated with a Lewis acid, a base, and substituted benzaldehyde III to yield alcohol IV with a high degree of stereoselectivity. Benzaldehyde III is substituted with ortho substituent Y which serves as a leaving group during cyclization step 4, group X (or X' for Scheme 2, in particular coupling step 4 of Scheme 2) which is substituted by the aryl sidechain during coupling step 6, and substituent $R^2$ which is as defined above. Substituent X (or X' for Scheme 2) is attached at position 4 or 5 of the phenyl moiety of benzaldehyde III. The leaving group Y is typically a halo or nitro group and X is a halide (and, for Scheme 2, X' is a halide or $C_1$-$C_4$ perfluoroalkylsulfonate). To prepare aldol product IV, acylated chiral auxiliary II is treated with a boron halide or sulfonate, such as a dialkylboron sulfonate, preferably dibutylboron triflate, in an aprotic solvent, such as dichloromethane, 1,2-dichloroethane, toluene, or diethyl ether, preferably dichloromethane, at a temperature of about −78 to 40° C., preferably −5° C., over a period of about 20 minutes, followed by treatment with a tertiary amine base, such as triethylamine or diisopropylethylamine, preferably triethylamine, at a temperature of about −78 to 40° C., preferably −5 to 5° C., over a period of about one hour. This mixture is treated with substituted benzaldehyde III at a temperature of about −100 to 0° C., preferably about −70° C., over a period of about 30 minutes. This mixture is allowed to warm to a temperature of about −20 to 25° C., preferably about −10° C., over a period of about one hour, and then treated with a protic oxidative quench, preferably by the successive addition of a pH 7 buffer solution, methanol, and aqueous hydrogen peroxide, at a temperature of less than about 15° C., to yield alcohol IV.

Step 2' of Scheme 1 is an alternative, and preferable, method of providing alcohol IV using a titanium-containing Lewis acid. In step 2' of Scheme 1, acylated chiral auxiliary II is treated with a titanium(IV) halide, preferably titanium tetrachloride, in an aprotic solvent such as dichloromethane, 1,2-dichloroethane, or toluene, preferably dichloromethane, at a temperature of about −80 to 0° C., preferably −80 to −70° C., over a period of about 30 minutes with additional stirring for about 30 minutes, followed by treatment with a tertiary amine or tertiary diamine base, such as triethylamine or N,N,N',N'-tetramethylethylenediamine, preferably N,N,N',N'-tetramethylethylenediamine, at a temperature of about −80 to 0° C., preferably −80 to −65° C., over a period of about 30 minutes. This is optionally, and preferably, followed by treatment with a donor ligand, such as 1-methyl-2-pyrrolidinone, dimethylformamide, 1,3-dimethyl-3,4,5,6-tetrahydro-2(1H)-pyrimidinone, triethylphosphate, or 2,2'-dipyridyl, preferably 1-methyl-2-pyrrolidinone, at a temperature of about −80 to 0° C., preferably −80 to −65° C., followed by stirring for a period of about 30 minutes. This mixture is treated with substituted benzaldehyde III at a temperature of about −100 to 0° C., preferably −80 to −65° C., over a period of about 30 minutes, and allowed to warm to a temperature of −30 to 30° C., preferably 0 to 25° C., over a period of about one to 24 hours, preferably about 4 hours. This mixture is treated with a protic quench, preferably aqueous ammonium chloride, at a temperature of −30 to 30° C., preferably 0 to 25° C., to yield alcohol IV. Where treatment with a donor ligand is done, the alcohol IV is, in some cases, provided as a crystalline solvate with the donor ligand. Stirring the quenched reaction mixture with a solid support such as Celite® for a period of about 12 hours at a temperature of about 20° C. improves the filtration of the reaction mixture for removal of titanium byproducts.

The titanium aldol conditions of step 2' of Scheme 1 are preferable and operationally more simple than the boron aldol conditions of step 2 of Scheme 1 in that they avoid the pyrophoric reagent tributylborane, the corrosive reagent triflic acid, and their exothermic combination in the preparation of the Lewis acid dibutylboron triflate. Further, in contrast to titanium aldol reactions described in the literature, such as in Evans, D. A.; Rieger, D. L.; Bilodeau, M. T.; Urpi, F., *J. Am. Chem. Soc.* 1991, 113, 1047, the titanium aldol conditions of step 2' of Scheme 1 provide high selectivity with less than two equivalents of the aldehyde III. Preferably, about one equivalent of aldehyde III is used in this step. The phrase "about one equivalent" as used herein in reference to aldehyde III or a compound of the formula $R^{11}C(O)H$ (as recited in the claims) means less than 1.5 equivalents of said compound. In the foregoing article by Evans et al., it is reported that two equivalents of aldehyde would be required for a titanium aldol reaction analogous to step 2' of Scheme 1.

In addition to having utility in the preparation of the therapeutic agents of formula X, the titanium aldol conditions of step 2' of Scheme 1 are useful in the preparation of HIV protease inhibitor compounds that are described in United Kingdom patent application number 2,270,914 (published Mar. 30, 1994) and in B. D. Dorsey et al., *Tetrahedron Letters*, 1993, 34(12), 1851. Scheme 4 illustrates the application of titanium aldol reaction to aldehyde XVIII in which $R^{11}$ is $C_1$–$C_9$ alkyl, $C_2$–$C_9$ alkenyl, or phenyl substituted by Y in the 2 position, X in the 4 or 5 position, and $R^2$ in one of the remaining positions of the phenyl moiety, wherein Y, X and $R^2$ are as defined above. The reaction conditions for Scheme 4 are the same as those described above for step 2' of Scheme 1. Aldehyde XVIII encompasses aldehyde III from Scheme 1, and alcohol XIX encompasses alcohol IV from Scheme 1. The reaction of Scheme 4 can be used to prepare the HIV protease inhibitor compounds that are described in United Kingdom patent application number 2,270,914, referred to above, where $R^{11}$ is $C_1$–$C_9$ alkyl or $C_2$–$C_9$ alkenyl, preferably 3-cyclohexylpropenyl.

Table 1 below illustrates how the product of Scheme 4 or step 2' of Scheme 1 can vary depending on the reaction conditions that are used, and, in particular, how the diastereoselectivity increases by increasing the amount TMEDA from 1.2 to 3 equivalents and by the addition of 2 equivalents of NMP. In Table 1, 1.0 equivalent of aldehyde RCHO was used for each reaction, x and y represent equivalents of base and NMP, respectively, NMP means 1-methyl-2-pyrrolidinone, TMEDA means N,N,N',N'-tetramethylethylenediamine, NEtiPr$_2$ means diisopropylethylamine, and the ratio of diastereomers was determined by HPLC. The aldol isomers were identified by separation and conversion to known carboxylic acid isomers by hydrolysis with LiOH/H$_2$O$_2$ according to procedures analogous to those described in Van Draanen, N. A.; Arseniyadis, S.; Crimmins, M. T.; Heathcock, C. H., *J. Org. Chem.* 1991, 56, 2499 and Gage, J. R.; Evans, D. A., Org. Svn. 1989, 68, 83. The desired isomer is indicated in bold.

SCHEME FOR TABLE 1

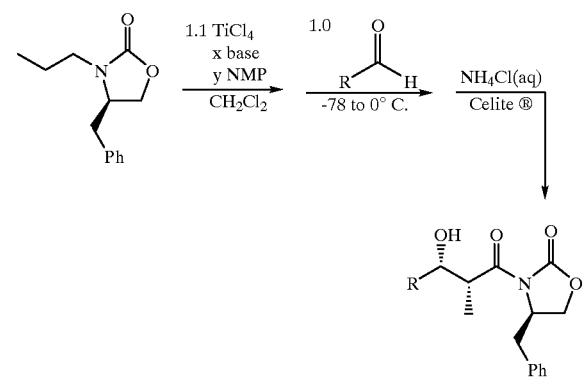

TABLE 1

| RCHO | x base | y NMP | enolization temperature | ratio of aldol diastereomers |
|---|---|---|---|---|
| ![benzaldehyde] | 1.2 NEtiPr$_2$ | 0 NMP | 0° C. | 33:—:2:65 (syn:anti:syn:anti) |
| " | 1.2 TMEDA | 0 NMP | 0° C. | 22:—:55:23 |
| " | 1.2 NEtiPr$_2$ | 0 NMP | −78° C. | 29:—:10:62 |
| " | 1.2 TMEDA | 0 NMP | −78° C. | 16:—:57:28 |
| " | 2 TMEDA | 0 NMP | −78° C. | 2:—:86:11 |
| " | 3 TMEDA | 0 NMP | −78° C. | 2:—:94:5 |
| " | 3 TMEDA | 2 NMP | −78° C. | 1:—:99:— |
| ![isobutyraldehyde] | 1.2 TMEDA | 0 NMP | −78° C. | —:—:11:89 (anti:anti:syn:syn) |
| " | 3 TMEDA | 2 NMP | −78° C. | —:—:—:100 |

TABLE 1-continued

| RCHO | x base | y NMP | enolization temperature | ratio of aldol diastereomers |
|---|---|---|---|---|
| pentanal (CH₃CH₂CH₂CH₂CHO) | 1.2 TMEDA | 0 NMP | −78° C. | 28:39:33:— |
| " | 3 TMEDA | 2 NMP | −78° C. | 4:92:3:2 |
| (E)-2-hexenal | 1.2 TMEDA | 0 NMP | −78° C. | 18:40:42:— |
| " | 3 TMEDA | 2 NMP | −78° C. | 2:96:2:— |

In step 3 of Scheme 1, chiral auxiliary $X_c$ is removed (and optionally recovered for reuse in step 1), and the oxidation state of compound IV (acid level) is reduced to the desired alcohol V according to a procedure analogous to the procedure described in Penning, T. D.; Djuric, S. W.; Haack, R. A.; Kalish, V. J.; Miyashiro, J. M.; Rowell, B. W.; Yu, S. S., *Syn. Commun.* 1990, 20, 307, which is incorporated herein by reference. In this process, alcohol IV is treated with a hydride reducing agent, such as lithium borohydride, lithium aluminum hydride, sodium borohydride, or calcium borohydride, preferably lithium borohydride, in an ethereal solvent such as THF, diisopropyl ether, or methyl tert-butyl ether, preferably THF, typically containing a protic solvent, such as water, ethanol, or isopropanol, at a temperature of about −78° C. to reflux temperature, preferably 0° C. to ambient temperature (20–25° C.). After a period of one to 24 hours, typically 12 hours, the reaction is quenched with water with the optional subsequent addition of hydrogen peroxide. Chiral auxiliary $HX_c$ can be recovered for reuse in step 1 by selective precipitation, or by extraction of $HX_c$ into aqueous acid, preferably hydrochloric acid, from a solution of diol V in an organic solvent such as diisopropyl ethyl or a mixture of ethyl acetate and hexane, followed by neutralization of the aqueous acidic extracts with base, and extraction of $HX_c$ into an organic solvent.

Step 4 of Scheme 1 is an intramolecular aromatic substitution whereby the primary hydroxyl in diol V displaces ortho leaving group Y to generate the chromanol ring system of VI. In particular, diol V, in which leaving group Y is a halo or nitro group, preferably a fluoro group, is treated with a base, such as potassium tert-butoxide, sodium bis(trimethylsilyl)amide, potassium bis(trimethylsilyl)amide, cesium carbonate, or sodium hydride, preferably potassium tert-butoxide, in an aprotic solvent such as THF, dimethyl sulfoxide, or 1-methyl-2-pyrrolidinone, preferably THF, optionally in the presence of added copper salts, at a temperature of between ambient temperature and 130° C., preferably about 70° C., for a period of one to 24 hours, typically about four hours, giving chromanol VI. In chromanol VI, the substituent X (or X' for Scheme 2) is attached at position 6 or 7 of the chroman ring.

In step 5 of Scheme 1, substituent X in chromanol VI is converted to lithium and then a boronic acid group. For lithiation, chromanol VI is preferably treated first with methyl lithium to form the lithium alkoxide followed by butyl lithium to form the aryl lithium. In this process, chromanol VI, in which X is a halide, preferably bromide or iodide, is treated with two equivalents of alkyllithium, preferably first with one equivalent of methyllithium followed by one equivalent of butyl lithium, in an ethereal solvent, preferably THF, at a temperature of −78 to 0° C., preferably −70 to −65° C., for a period of about one hour, followed by treatment with a borating agent, such as borane-tetrahydrofuran complex, triisopropyl borate, or trimethyl borate, preferably borane-THF complex, at a temperature of −78 to 0° C., preferably −70 to −65° C., over a period of about 30 minutes, followed by quenching with water or optionally aqueous acid at a temperature of about −65° C. to ambient temperature, preferably at about 0° C., giving boronic acid VII in which the boronic acid moiety is attached at position 6 or 7 of the chroman ring.

Step 6 of Scheme 1 is a Suzuki coupling between boronic acid VII and compound VIII to form the biaryl bond of compound IX. In compound VIII, Z is a halide or sulfonate, preferably bromide, iodide, or trifluoromethanesulfonate, $R^4$ is $C_1$–$C_6$ alkyl and $R^3$ is as defined above. This procedure is analogous to the procedure described in Miyaura, N.; Suzuki, A., *Chem. Rev.* 1995, 95, 2457, which is incorporated herein by reference. This procedure is preferable to the coupling of zinc or tin species due to the difficulty of preparing organozincs on a large scale and the toxicity of organotin compounds. In this process, a mixture of boronic acid VII, arene VIII, a palladium catalyst, such as tetrakis(triphenylphosphine)palladium(0), dichlorobis(triphenylphosphine)palladium(II), palladium(II) acetate, allylpalladium chloride dimer, tris(dibenzylideneacetone)dipalladium(0), or 10% palladium on carbon, preferably 10% palladium on carbon, and a base or fluoride salt, such as sodium carbonate, triethylamine, sodium bicarbonate, cesium carbonate, tripotassium phosphate, potassium fluoride, cesium fluoride, or tetrabutylammonium fluoride, preferably potassium fluoride, in a solvent such as ethanol, dimethoxyethane, or toluene, optionally containing water, preferably ethanol, are stirred at a temperature of between ambient temperature and 130° C., preferably reflux temperature, for a period of about one to about 24 hours, preferably about three hours, giving biaryl IX in which the benzyl ester moiety is attached at position 6 or 7 of the chroman ring.

In step 7 of Scheme 1, ester IX is treated with aqueous hydroxide base, such as aqueous sodium hydroxide, in an alcoholic solvent, such as isopropyl alcohol, at a temperature of between 40° C. and reflux temperature, preferably reflux temperature, for a period of about one to about 24 hours, preferably about six hours. The reaction mixture is cooled to ambient temperature and partitioned between aqueous base and an organic solvent, such as a mixture of hexane and isopropyl ether. The aqueous solution is acidified, and the final compound X is extracted into an organic solvent such as ethyl acetate. This method of extracting the compound X with organic solvents removes neutral impurities which is particularly advantageous in the last step of this synthesis.

To facilitate the handling of carboxylic acid X, this compound can be treated with a secondary amine of the formula $NHR^5R^6$, wherein $R^5$ and $R^6$ are as defined above, in a solvent such as toluene, to form an ammonium carboxylate of the formula

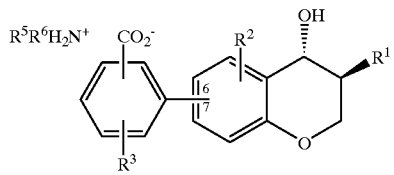

XVII wherein $R^1$, $R^2$, $R^3$, $R^5$ and $R^6$ are as defined above. Ammonium carboxylate XVII can be treated with an aqueous acid such a hydrochloric acid or sulphuric acid, preferably hydrochloric acid, in a solvent such as ethyl acetate, toluene, or methylene chloride, preferably ethyl acetate, at a temperature ranging from 0° C. to ambient temperature for a period of 30 minutes to 3 hours, preferably 1 hour, to provide carboxylic acid X.

Scheme 2 illustrates an alternative to the coupling sequence of steps 5 and 6 of Scheme 1. The process of Scheme 2 is preferred. Step 1 of Scheme 2 is an esterification of carboxylic acid XI with alcohol $R^4OH$, in which $R^3$ and $R^4$ are as defined above, to generate ester XII. In this process, carboxylic acid XI is treated with alcohol $R^4OH$, preferably a primary or secondary alcohol such as 2,2-dimethyl-propyl alcohol, and an acid such as sulfuric acid, hydrochloric acid, methanesulfonic acid, toluenesulfonic acid, or camphor sulfonic acid, preferably sulfuric acid, in a solvent such as toluene, dichloromethane, or dichloroethane, preferably toluene, at a temperature of 0° C. to reflux temperature, preferably reflux temperature, for a period of one to 24 hours, typically 4 hours, to provide ester XII.

In step 2 of Scheme 2, ester XII is treated with a base and the resulting ortho metallated species is trapped with a trialkylborate to give boronate ester XIII. In step 3 of Scheme 2, the boronate ester XIII is hydrolyzed to the corresponding boronic acid XIV which is performed by methods known to those skilled in the art. In steps 2 and 3 of Scheme 2, ester XII is treated with a metal amide base such as lithium diisopropylamide, lithium diethylamide, lithium 2,2,6,6-tetramethylpiperidine, or bis(2,2,6,6-tetramethylpiperidino)magnesium, preferably lithium diisopropylamide, in the presence of a tri-($C_1$–$C_4$ alkyl) borate, such as triisopropylborate, triethylborate, or trimethylborate, preferably triisopropylborate, in an ethereal solvent, such as THF, diisopropyl ether, dioxane, or methyl tert-butyl ether, preferably THF, over a temperature range of about –78° C. to ambient temperature (20–25° C.), preferably about 0° C. After a period of 10 minutes to 5 hours, typically 1 hour, the reaction is quenched with aqueous acid to provide boronic acid XIV.

To facilite the handling of boronic acid XIV before proceeding to step 4 of Scheme 2, the boronic acid XIV can be reacted with an aminodiol as illustrated in Scheme 3. In Scheme 3, boronic acid XIV is reacted with aminodiol XV, wherein $R^8$, m and n are as defined above, in a solvent such as isopropanol, ethanol, methanol, hexanes, toluene, or a combination of the foregoing solvents, preferably isopropanol, at a temperature within the range of 0° C. to reflux temperature, preferably ambient temperature, for a period of 15 minutes to 10 hours, preferably 10 hours, to provide the amine complex XVI. To proceed with step 4 of Scheme 2, amine complex XV is hydrolyzed to boronic acid XIV according to methods known to those skilled in the art. Such methods include the use of aqueous acid, such as hydrochloric acid.

Step 4 of Scheme 2 is a Suzuki coupling between boronic acid XIV and chromanol VI to form the biaryl bound of IX. In this process, a mixture is prepared containing boronic acid XIV, chromanol VI, a palladium catalyst, such as tetrakis (triphenylphosphine)palladium(0), dichlorobis (triphenylphosphine)palladium(II), palladium(II) acetate, allylpailadium chloride dimer, tris(dibenzylideneacetone) dipalladium(0), or 10% palladium on carbon, preferably tetrakis(triphenylphosphine)palladium(0), a base or fluoride salt, such as sodium carbonate, triethylamine, sodium bicarbonate, cesium carbonate, tripotassium phosphate, pottasium fluoride, cesium fluoride, sodium hydroxide, barium hydroxide, or tetrabutylammonium fluoride, preferably sodium carbonate, and a solvent such as toluene, ethanol, dimethoxyethane, optionally containing water, preferably toluene containing water. In chromanol VI, which is prepared according to Scheme 1, X', which is attached at position 6 or 7 of the chroman ring, represents a halide or $C_1$–$C_4$ perfluoroalkylsulfonate, preferably bromide, iodide, or trifluoromethanesulfonate. The mixture is stirred at a temperature of between ambient temperature and reflux temperature, preferably reflux temperature, for a period of about 10 minutes to about 6 hours, preferably 1 hour, to provide biaryl IX.

In step 5 of Scheme 2, ester IX is hydrolyzed to provide the carboxylic acid X as described above for step 7 of Scheme 1.

The present invention is illustrated by the following examples, but it is not limited to the details thereof. In the following examples, the term "ambient temperature" means a temperature within the range of about 20° C. to about 25° C.

EXAMPLE 1

(R)-4-Benzyl-3-(3-phenyl-propionyl)-oxazolidin-2-one

To a solution of (R)-(+)-4-benzyl-2-oxazolidinone (910 g, 5.14 mol) and 500 mg of 2,2'-dipyridyl as an indicator in tetrahydrofuran (9 L) at –78° C. was added over 30 minutes a 2.5 M solution of BuLi in hexanes (2.03 L, 5.14 mol). The temperature of the reaction mixture was maintained at less than –55° C. during the addition. The reaction mixture was cooled to –75° C. and hydrocinnamoyl chloride (950 g, 5.63 mol) was added over 5 minutes. The reaction mixture was allowed to warm to 0° C., at which point the reaction mixture was judged to be complete by thin layer chromatography (hexanes/ethyl acetate, 2:1). The reaction was quenched by adding 10% aqueous sodium bicarbonate (3.6 L) and water (3.6 L). The aqueous phase was separated and extracted with ethyl acetate (3 L). The combined organic layers were washed with 5% aqueous sodium carbonate (3.6 L) and saturated aqueous sodium chloride (2 L), dried over magnesium sulfate, and concentrated in vacuo to approximately 2 L of a viscous yellow suspension. This slurry was dissolved in ethyl acetate (3 L), concentrated to a solid, and dissolved in ethyl acetate at 50° C. Hexanes (10.7 L) was added, and the mixture was slowly cooled to 10° C. resulting in the precipitation of solids which were stirred at 10° C. for 30 minutes. The solids were collected by filtration, washed with hexanes, and air-dried at ambient temperature yielding 1.4 kg (88%) of (R)-4-benzyl-3-(3-phenyl-propionyl)-oxazolidin-2-one as pale yellow needles: $^1$H NMR (300 MHz, CDCl$_3$) δ7.14–7.33 (m, 10H), 4.66 (m, 1H), 4.17 (t, J=3.4 Hz, 2H), 3.26 (m, 3H), 3.03 (t, J=7 Hz, 2H), 2.75 (dd, J=9.5, 13.4 Hz, 1H); IR 1787, 1761, 1699, 1390, 1375, 1308, 1208, 1203, 746, 699 cm$^{-1}$; mp 102–104° C.

EXAMPLE 2

[4R-[3(2R,3R)]]-4-Benzyl-3-[2-benzyl-3-(4-bromo-2-fluoro-phenyl)-3-hydroxy-propionyl]-oxazolidin-2-one To a solution of (R)-4-benzyl-3-(3-phenyl-propionyl)-oxazolidin-2-one (1064 g, 3.44 mol) in dichloromethane (5.6 L) at −5° C. was added dibutylboron triflate (1133 g, 4.13 mol) over 15 minutes, followed by the addition of triethylamine (719 mL, 5.16 mol) while maintaining a reaction temperature of less than 5° C. This mixture was cooled to −70° C., and a solution of 4-bromo-2-fluoro-benzaldehyde (699 g, 3.44 mol) in dichloromethane (2 L) was added over 30 minutes. The mixture was allowed to warm to −10° C. over 1 hour, at which point it was judged to be complete by thin layer chromatography (hexanes/ethyl acetate, 2:1). The reaction was quenched by adding potassium phosphate monobasic-sodium hydroxide pH 7 buffer (3.5 L) over 30 minutes followed by methanol (1.8 L) and 35% aqueous hydrogen peroxide (1.8 L) over 1.5 hours while maintaining a reaction temperature of less than 15° C. The organic layer was separated, washed with saturated aqueous sodium bicarbonate (6.7 L), and diluted with anhydrous ethanol (4 L) and 25% aqueous sodium bisulfite. The organic layer was separated, washed with water (4 L), dried over magnesium sulfate, and concentrated in vacuo giving 1818 g (103%-crude weight) of [4R-[3(2R,3R)]]-4-benzyl-3-[2-(4-bromo-2-fluoro-phenyl)-3-hydroxy-propionyl]-oxazolidin-2-one as a very viscous amber-colored oil: $^1$H NMR (400 MHz, CDCl$_3$) δ7.46 (t, J=8.0 Hz,1H), 7.16–7.32 (m, 10H), 6.94–6.96 (m, 2H), 5.35 (d, J=4.7 Hz, 1H), 4.92–5.29 (m, 1H), 4.45–4.51 (m, 1H), 3.92 (m, 2H), 3.01 –3.14 (m, 3H), 2.83 (dd, J=3.1, 13.6 Hz, 1H), 2.05 (dd, J=10.0, 13.5 Hz, 1H); IR 3460 (br), 1780, 1696, 1483, 1388, 1350, 1209, 1106, 1068, 877, 760, 747, 701, 583, 512, 486 cm$^{-1}$.

EXAMPLE 3

[4R-[3(2R,3R)]]-4-Benzyl-3-[2-benzyl-3-(4-bromo-2-fluoro-phenyl)-3-hydroxy-propionyl]-oxazolidin-2-one, 1-Methyl-2-pyrrolidinone Solvate To a solution of (R)-4-benzyl-3-(3-phenyl-propionyl)-oxazolidin-2-one(12.0 kg, 38.8 mol) in dichloromethane (180 L) at −70° C. to −80° C. was added titanium tetrachloride (8.8 kg, 46.6 mol) over 30 minutes giving a thick suspension which was stirred for an additional 30 minutes at −70° C. to −80° C. N,N,N',N'-Tetramethylethylenediamine (17.6 L, 116.4 mol) was added over 30 minutes giving a more fluid reaction mixture. 1-Methyl-2-pyrrolidinone (7.6 kg, 77.6 mol) was added, and the reaction mixture was stirred for 30 minutes, all while maintaining a reaction temperature of less than −65° C. A solution of 4-bromo-2-fluoro-benzaldehyde (7.9 kg, 38.8 mol) in dichloromethane (38 L) was added over 30 minutes while maintaining a reaction temperature of less than or equal to −68° C. The reaction mixture was allowed to warm to 20° C. over 8 hours at which point it was cooled to 10° C. and quenched with a solution of 5.0 kg of ammonium chloride in 11 L of water inducing a white precipitate and an exotherm to 28° C. Celite® (12 kg) was added and the reaction mixture was stirred for 12 hours at 20° C. The reaction mixture was filtered, concentrated atmospherically to an oil, treated with hexanes (120 L), concentrated to approximately 50 L, slowly cooled to 0° C. and granulated for 24 hours. The crude product, 24.3 kg, was isolated by filtration, combined with the crude products from two similar reactions in 110 L of dichloromethane, treated with 320 L of hexanes, concentrated atmospherically to a final volume of approximately 250 L (distillate temperature 65° C.), seeded with authentic product, and slowly cooled with granulation over 18 hours at 20° C. Filtration yielded 67.4 kg (94%) of [4R-[3(2R,3R)]]-4-benzyl-3-[2-benzyl-3-(4-bromo-2-fluoro-phenyl)-3-hydroxy-propionyl]-oxazolidin-2-one, 1-methyl-2-pyrrolidinone solvate as a light tan granular solid: $^1$H NMR (400 MHz, CDCl$_3$) δ7.46 (t, J=8.0 Hz, 1H), 7.15–7.29 (m, 10H), 6.94 (dd, J=1.9, 7.2 Hz, 2H), 5.34 (d, J=4.8 Hz, 1H), 4.91–4.96 (m, 1H), 4.44–4.49 (m, 1H), 3.90–3.95 (m, 2H), 3.55 (bs, 1H), 337 (dd, J=7.2, 7.2 Hz, 2H), 3.00–3.13 (m, 2H), 2.83 (s, 3H), 2.82 (dd, J=3.3, 13.3 Hz, 1H), 2.36 (dd, J=8.2, 8.2 Hz, 2H), 1.97–2.06 (m, 3H); IR 3150 (br), 1776, 1695, 1652, 1600, 1221, 1050, 996, 953, 875 cm$^{-1}$; mp 80–83° C.

EXAMPLE 4

(1R,2S)-2-Benzyl-1-(4-bromo-2-fluoro-phenyl)-propane-1,3-diol

A 2 M solution of lithium borohydride in tetrahydrofuran (1.7 L, 3.4 mol) was diluted with tetrahydrofuran (1.7 L) and cautiously treated with water (61 mL, 3.4 mol) over 15 minutes. This mixture was stirred at ambient temperature until hydrogen evolution ceased (0.5 to 1 hour), and then added to a solution of [4R-[3(2R,3R)]]-4-benzyl-3-[2-benzyl-3-(4-bromo-2-fluoro-phenyl)-3-hydroxy-propionyl]-oxazolidin-2-one (1.75 kg, 3.4 mol) in tetrahydrofuran (8.75 L) at 0° C. over 30 minutes. The resulting milky-white suspension was allowed to warm to ambient temperature over 12 hours at which point it was judged to be complete by thin layer chromatography (hexanes/ethyl acetate, 2:1). The reaction mixture was cooled to 15° C. and quenched with water (5.25 L) over 15 minutes and stirred an additional 10 minutes before adding 35% aqueous hydrogen peroxide (2.6 L) over 20 minutes. The reaction mixture was stirred for 15 minutes and then diluted with ethyl acetate (5.3 L) and water (4 L). The organic layer was separated and washed with water (5.3 L), 5% aqueous sodium bisulfite (5.25 L), and 50% saturated aqueous sodium chloride (7.5 L). Peroxides were detected in the organic layer, so it was further washed with 5% aqueous sodium bisulfite (5 L) and 50% saturated aqueous sodium chloride (6 L). The organic layer was concentrated in vacuo to an oil, diluted with ethyl acetate (4 L) and hexanes (13 L), and washed with 1 N aqueous hydrochloric acid (6 times 17 L) to remove the (R)-(+)-4-benzyl-2-oxazolidinone. The organic layer was washed with saturated aqueous sodium bicarbonate (5.3 L), diluted with toluene (2 L), and concentrated in vacuo yielding 1138 g (98%) of (1R,2S)-2-benzyl-1-(4-bromo-2-fluoro-phenyl)-propane-1,3-diol as an oil: $^1$H NMR (400 MHz, CDCl$_3$) δ7.47–7.51 (m, 1H), 7.33 (dd, J=1.9, 8.3 Hz, 1H), 7.15–7.25 (m, 4H), 7.04–7.06 (m, 2H), 5.39 (d, J=2.6 Hz, 1H), 3.77 (dd, J=3.0, 10.7 Hz, 1H), 3.64 (dd, J=5.0, 10.8 Hz, 1H), 3.44 (bs, 1H), 2.68 (dd, J=11.0, 13.8 Hz, 1H), 2.59 (dd, J=4.1, 13.9 Hz, 1H), 2.15–2.20(m, 1H), 2.01 (bs, 1H); IR 3370 (br), 3269 (br), 1485, 1406, 1213,1033,1021,870,700 cm$^{-1}$.

EXAMPLE 5

(3S,4R)-3-Benzyl-7-bromo-chroman-4-ol

A 1 M solution of sodium bis(trimethylsilyl)amide in tetrahydrofuran (6.55 L, 6.55 mol) was added over 20 minutes to a solution of (1R,2S)-2-benzyl-1-(4-bromo-2-fluoro-phenyl)-propane-1,3-diol (1975 g, 5.82 mol) in dimethyl sulfoxide (9.88 L) at ambient temperature. The mixture was slowly heated to 60° C. under aspirator vacuum to displace the tetrahydrofuran from the reaction mixture, and then heated at 60 to 65° C. for 5 hours under aspirator vacuum at which point the reaction was judged to be complete according to thin layer chromatography (hexanes/ethyl acetate, 2:1). The reaction mixture was cooled to ambient temperature and quenched by adding water (10 L) followed by 1 N aqueous hydrochloric acid (10 L). The resulting tan suspension was filtered, washed with water (2 L), and dissolved in ethyl acetate (12 L). This solution was washed with water (two times 12 L), concentrated to a low volume, dissolved in isopropyl ether (4 L), and concentrated under atmospheric pressure at 50 to 60° C. to 1.0 L, at which point solids began to precipitate. The resulting suspension was cooled to ambient temperature, stirred for 12 hours, concentrated to one-half its volume, cooled to 0 to 5° C., and filtered giving 916 g (49%) of (3S,4R)-3-benzyl-7-bromo-chroman-4-ol as a white solid. The filtrate was concentrated to a dark oil (906 g), dissolved in isopropyl ether (1.5 L) at reflux, cooled to ambient temperature, stirred, and filtered yielding an additional 82 g of solid. The filtrate was concentrated and chromatographed on silica gel (60–230 mesh) eluting with 3:1 hexanes/ethyl acetate. Product-rich fractions were concentrated and recrystallized from isopropyl ether yielding an additional 82 g of solid. The total yield of (3S,4R)-3-benzyl-7-bromo-chroman-4-ol was 1080 g (58%): $^1$H NMR (400 MHz, CDCl$_3$) δ7.29–7.33 (m, 2H), 7.21–7.25 (m, 1H), 7.15–7.19(m, 3H), 7.06–7.09 (m, 2H), 4.44 (bs, 1H), 4.21 (dd, J=2.6, 11.3 Hz, 1H), 3.97 (dd, J=4.5, 11.3 Hz, 1H), 2.68 (dd, J=6.5, 13.8 Hz, 1H), 2.51 (dd, J=9.1, 13.8 Hz, 1H), 2.18–2.23 (m, 1H), 1.85 (d, J=4.3 Hz, 1H); IR 3274 (br), 3181 (br), 1598, 1573, 1493, 1480, 1410, 1219, 1070, 1052, 1023, 859, 700 cm$^{-1}$; mp 143.5–144.0° C.

EXAMPLE 6

(3S,4R)-3-Benzyl-7-bromo-chroman-4-ol

To a solution of (1R,2S)-2-benzyl-1-(4-bromo-2-fluoro-phenyl)-propane-1,3-diol (prepared from 33.5 kg (54.8 moles) of [4R-[3(2R,3R)]]-4-benzyl-3-[2-benzyl-3-(4-bromo-2-fluoro-phenyl)-3-hydroxy-propionyl]-oxazolidin-2-one, 1-methyl-2-pyrrolidinone solvate without isolation) in 185 L of tetrahydrofuran was added 12.9 kg (115 mol) of potassium tert-butoxide. The reaction mixture was heated at reflux for 4 hours at which point the reaction was found to be complete by thin layer chromatography (hexanes/ethyl acetate, 3:1). The reaction mixture was cooled to ambient temperature, quenched with 170 L of water, diluted with 83 L of ethyl acetate, and acidified to pH 5.3 (aqueous layer) with 7.5 L of concentrated hydrochloric acid. The organic layer was concentrated under vacuum to approximately 38 L of a slurry, diluted with 76 L of isopropyl ether, warmed to dissolve the solids, slowly cooled to 0° C., and granulated at 0° C. for 12 hours. (3S,4R)-3-Benzyl-7-bromo-chroman-4-ol, 5.1 kg of white solid, was isolated by filtration. The mother liquor was washed with 4 L of saturated aqueous sodium chloride, concentrated to a final volume of 57 L, and granulated at 0° C. for 12 hours affording a 4.3 kg second crop of (3S,4R)-3-benzyl-7-bromo-chroman-4-ol.

A second identical reaction mixture was quenched, diluted with ethyl acetate, and acidified as described above. The organic layer was dried over 10 kg of magnesium sulfate, concentrated atmospherically to approximately 30 L of a slurry, diluted with 38 L of isopropyl ether, concentrated to approximately 57 L, slowly cooled, and granulated at 0to 10° C. for 12 hours. (3S,4R)-3-Benzyl-7-bromo-chroman-4-ol, 8.7 kg, was isolated by filtration. The mother liquor was combined with the mother liquor from the second crop from the first reaction, concentrated to an oil, solidified by cooling, granulated in 6 L of isopropyl ether at 20° C. for 12 hours and 0° C. for 2 hours, and filtered giving 6.3 kg of (3S,4R)-3-benzyl-7-bromo-chroman-4-ol after washing with cold isopropyl ether. The combined crops from both reactions were dried giving 20.8 kg (59%) of (3S,4R)-3-benzyl-7-bromo-chroman-4-ol.

EXAMPLE 7

(3S,4R)-(3-Benzyl-4-hydroxy-chroman-7-yl)-boronic Acid

To a solution of (3S,4R)-3-benzyl-7-bromo-chroman-4-ol (377 g, 1.18 mol) in tetrahydrofuran (5.6 L) at −75° C. was added a 1.48 M solution of methyllithium in ether (1.6 L, 2.37 mol) over 45 minutes while maintaining a temperature of less than −65° C. The reaction mixture was stirred at less than −65° C. for 1 hour, followed by the addition of a 2.5 M solution of butyllithium in hexanes (440 mL, 1.3 mol) over 15 minutes. The reaction mixture was stirred at less than −65° C. for 1 hour, followed by the addition of a 1.0 M solution of borane-tetrahydrofuran complex in tetrahydrofuran (5.9 L, 5.9 mol) over 30 minutes. The reaction mixture was warmed to 0° C., quenched by adding water (4.4 L), adjusted to pH 2 with 1 N aqueous hydrochloric acid (4 L), and extracted with isopropyl ether (4 L). The aqueous layer was extracted with isopropyl ether (4 L), and the combined organic layers were washed with 0.5 N aqueous sodium hydroxide (7.2 L). The aqueous layer was adjusted to pH 3 with 1 N aqueous hydrochloric acid (5.5 L) and extracted with ethyl acetate (5.4 L and 2.7 L). The combined ethyl acetate layers were dried over magnesium sulfate, and concentrated in vacuo yielding 304.5 g (91%) of (3S,4R)-(3-benzyl-4-hydroxy-chroman-7-yl)-boronicacid as a yellow foam: $^1$H NMR (300 MHz, CDCl$_3$) δ7.35–7.00 (m, 8H), 4.42 (d, J=4.1 Hz, 1H), 4.19 (d, J=1H), 3.90 (m, 1H), 2.68 (dd, J=6.2, 13.8 Hz, 1H), 2.47 (m, 1H), 2.15 (m, 1H); IR 3330 (br), 1413, 1348, 1320, 1211, 1025, 749, 730, 700 c$^{-1}$.

EXAMPLE 8

(3S,4R)-2-(3-Benzyl-4-hydroxy-chroman-7-yl)-4-trifluoromethyl-benzoic Acid Ethyl Ester A mixture of ethyl 2-iodo-4-trifluoromethyl-benzoate (723 g, 2.1 mol), (3S,4R)-(3-benzyl-4-hydroxy-chroman-7-yl)-boronic acid (627 g, 2.2 mol), potassium fluoride (366 g, 6.3 mol), 10% palladium on carbon (157 g, 50% water wet), and anhydrous ethanol (6.27 L) was heated at reflux for 3 hours at which point thin layer chromatography (toluene/acetic acid, 5:1) indicated the reaction to be complete. The reaction mixture was diluted with isopropyl ether (8 L), filtered through Celiteand washed with 10% aqueous sodium bicarbonate (1.5 L). The aqueous layer was separated and extracted with isopropyl ether (3 L). The combined organic layers were washed with water (6 L), dried over magnesium sulfate, and treated with Darco®G-60 (1.0 kg) and silica gel (1 kg, 70–230 mesh) at ambient temperature. This mixture was filtered through a pad of silica gel (70–230 mesh) and concentrated in vacuo to 922 g of dark oil. This oil was diluted with ethyl acetate (1 L) and filtered through a column of silica gel (2 kg) eluting with ethyl acetate giving a light amber solution which was concentrated to afford 897 g (92%) of (3S,4R)-2-(3-benzyl-4-hydroxy-chroman-7-yl)-4-trifluoromethyl-benzoicacid ethyl ester as a light amber oil: $^1$H NMR (400 MHz, CDCl$_3$) δ7.89 (d, J=8.1 Hz, 1H), 7.63–7.67 (m, 2H), 7.18–7.38 (m, 6H), 6.91 (dd, J=1.8, 7.8 Hz, 1H), 6.86 (d, J=1.7 Hz, 1H), 4.55 (bs, 1H), 4.25 (dd, J=2.7, 11.2 Hz, 1H), 4.17 (q, J=7.1 Hz, 2H), 4.00 (ddd, J=1.0, 4.5,11.2 Hz, 1H), 2.75 (dd, J=6.4, 13.9 Hz, 1H), 2.56 (dd, J=9.3, 13.8 Hz, 1H), 2.26 (m, 1H), 1.93 (d, J=4.3 Hz, 1H), 1.09 (t, J=7.2 Hz, 3H); IR 3307 (br), 3216 (br), 1734, 1339, 1298, 1247, 1191, 1175, 1118, 1097, 1050 cm$^{-1}$.

EXAMPLE 9

(3S,4R)-2-(3-Benzyl-4-hydroxy-chroman-7-yl)-4-trifluoromethyl-benzoic Acid

A mixture of (3S,4R)-2-(3-benzyl-4-hydroxy-chroman-7-yl)-4-trifluoromethyl-benzoic acid ethyl ester (897 g, 1.93 mol) and 10% aqueous sodium hydroxide (980 mL, 2.72 mol) in isopropyl alcohol (9 L) was heated at reflux for 6 hours, cooled to ambient temperature, and stirred for 12 hours. The reaction mixture was diluted with water (13.5 L), hexanes (9 L), and isopropyl ether (4.5 L). The aqueous layer was separated and extracted with hexanes (9 L) and isopropyl ether (4.5 L), adjusted to pH 2 with 2 N aqueous hydrochloric acid, and extracted with ethyl acetate (8 L and 4 L). The combined ethyl acetate extracts were washed with water (6 L), dried over magnesium sulfate, and concentrated in vacuo to a dark amber oil which was diluted with toluene (2 L) and concentrated again to an oil. The oil was dissolved in toluene (4.2 L) at 60° C., and hexanes (8.8 L) were added at a rate to maintain a temperature of greater than 50° C. The tan solids which precipitated upon slowly cooling to ambient temperature over several hours were filtered and washed with 2:1 hexane/toluene (2 L). These solids were dissolved in toluene (5 L) at 60° C., treated with Darco®G-60, filtered, washed with toluene, and concentrated in vacuo to approximately 4.0 L. This mixture was heated to 50–60° C., treated drop-wise with hexanes(8.6 L), cooled, and granulated at 5° C. for 1 to 2 hours. The resulting solids were filtered, washed with 2:1 hexanes/toluene (2 L), and the wet cake was stirred with hexanes (4 L) at reflux for 30 minutes. This mixture was cooled to ambient temperature, granulated for 1 hour, filtered, and the resulting solids were dried under vacuum overnight to provide 450 g (55%) of (3S,4R)-2-(3-benzyl-4-hydroxy-chroman-7-yl)-4-trifluoromethyl-benzoicacid as an off white solid: $^1$H NMR (400 MHz, CDCl$_3$) δ7.99 (d, J=8.1 Hz, 1H), 7.66 (dd, J=1.1, 8.1 Hz, 1H), 7.63 (s, 1H), 7.15–7.32 (m, 6H), 6.89 (dd, J=1.7, 7.9 Hz, 1H), 6.85 (d, J=1.7 Hz, 1H), 6.1 (bs, 2H), 4.50 (d, J=4.3 Hz, 1H), 4.1 8 (dd, J=2.7, 11.2 Hz, 1H), 3.94 (dd, J=4.6, 11.0 Hz, 1H), 2.74 (dd, J=6.1, 13.8 Hz, 1H), 2.51 (dd, J=9.4, 13.9 Hz, 1H),2.22 (m,1H); IR 3454,3218 (br), 1699, 1431, 1337, 1299, 1275, 1258, 1191, 1178, 1135, 1123, 700 cm$^{-1}$; mp 142° C.

EXAMPLE 10

4-Trifluoromethyl-benzoic Acid 2,2-Dimethyl-propyl Ester

To a suspension of 4-trifluoromethylbenzoic acid (75.0 g, 394 mmol) and 2,2-dimethyl-propyl alcohol (70.5 g, 800 mmol) in toluene (500 mL) was added concentrated sulfuric acid (3.0 mL). The mixture was stirred at reflux for 4 hours, cooled to room temperature, poured into saturated aqueous sodium carbonate (250 mL) and the layers were separated. The organic layer was washed with saturated aqueous sodium carbonate (250 mL), and brine (100 mL), and was concentrated to give 4-trifluoromethyl-benzoic acid, 2,2-dimethyl-propyl ester (102 g, 99% yield) as a yellow liquid: R$_f$: 0.66 (ethyl acetate/hexanes 25/75); IR 2932, 1727, 1327, 1280, 1133, 1066, 862, 775, 704 cm$^{-1}$; $^1$H NMR (400 MHz, CDCl$_3$) δ8.16 (d, J=7.9 Hz, 2H), 7.70 (d, J=8.1 Hz, 2H), 4.04 (s, 2H), 1.04 (s, 9); $^{13}$C NMR (100 MHz, CDCl$_3$) δ26.51, 31.61, 74.72, 123.63 (q, J=272.7 HZ), 125.4, 129.9, 133.7, 134.35 (q, J=31.7 Hz), 165.35.

EXAMPLE 11

2-(2,2-Dimethyl-propoxycarbonyl)-5-trifluoromethyl-benzeneboronic Acid

To a solution of 4-trifluoromethyl-benzoic acid 2,2-dimethyl-propyl ester (4.225 g, 16.23 mmol) in tetrahydrofuran (40 mL) was added triisopropylborate (9.00 mL, 39.0 mmol). The solution was cooled to −78° C. and lithium diisopropylamide (12.0 mL of a 2.0 M solution in tetrahydrofuran/heptane, 24.0 mmol) was added dropwise over 5 minutes. The red solution was stirred for 30 minutes, warmed to 0° C., and quenched by the slow addition of 1N hydrochloric acid (50 mL). The mixture was allowed to warm to room temperature, stirred for 30 minutes and added to hexanes (200 mL). The layers were separated and the organic layer was washed successively with 2N hydrochloric acid (two times with 100 mL), water (100 mL), and brine (50 mL). The organic extracts were dried over magnesium sulfate, filtered, and concentrated to an oil. The crude product was crystallized from heptane (40 mL) to provide 2-(2,2-dimethyl-propoxycarbonyl)-5-trifluoromethyl-benzeneboronic acid (3.037 g, 62% yield) as a white solid: mp=159–160° C.; IR 3377 (br), 2963, 1703, 1371, 1308, 1171, 1131, 794, 709 cm$^{-1}$; $^1$H NMR (400 MHz, DMSO/D$_2$O) δ8.05 (d, J=8.1 Hz, 1H), 7.78 (d, J=8.3 Hz, 1H), 7.66 (s, 1H), 3.94 (s, 2H), 0.95 (s, 9H); $^{13}$C NMR (100 MHz, DMSO/D$_2$O) δ26.69, 31.69, 74.91, 125.29, 125.75, 128.30, 129.62, 131.98 (q, J=31.8 Hz), 136.28, 142.68,166.90.

EXAMPLE 12

(3S,4R)-2-(3-Benzyl-4-hydroxy-chroman-7-yl)-4-trifluoromethyl-benzoic Acid 2,2-Dimethyl-propyl Ester A bi-phasic solution of 2-(2,2-dimethyl-propoxycarbonyl)-5-trifluoromethyl-benzeneboronic acid (1.72 g, 5.66 mmol), (3S,4R)-3-benzyl-7-bromo-chroman-4-ol(1.80 g, 5.63 mmol), sodium carbonate (1.82 g, 17.2 mmol), and tretrakis (triphenyl-phosphine)palladium(0) (12 mg, 0.19 mol %) in toluene (15 mL) and water (9 mL) was stirred at reflux for 100 minutes. The reaction mixture was cooled to room temperature, poured into water (40 mL) and extracted with diisopropylether (75 mL). The organic extracts were washed with brine (50 mL), treated with Darco® G-60, dried over magnesium sulfate, filtered through Celite®, and concentrated. The crude product was purified by chromatography on silica gel (ethyl acetate/hexanes 20/80) to provide (3S,4R)-2-(3-benzyl-4-hydroxy-chroman-7-yl)-4-trifluoromethyl-benzoic acid 2,2-dimethylpropyl ester as a white foam (2.35 g, 84% yield): R$_f$: 0.32 (ethyl acetate/hexanes25/75); IR 3407 (br), 2961, 1721, 1336, 1292, 1252, 1172, 1134, 1110, 1022, 848, 749 cm$^{-1}$; $^1$H NMR (400 MHz, CDCl$_3$) δ7.90 (d, J=8.1 Hz, 1H), 7.66 (d, J=8.1 Hz, 1H), 7.63 (s, 1H), 7.19–7.37 (m, 6H), 6.88–6.93 (m, 2H), 4.53 (t,J=4.4 Hz, 1H), 4.22 (dd, J=11.2, 2.5 Hz, 1H), 3.99 (dd, J=11.2, 3.3 Hz, 1H), 3.78 (s, 2H), 2.73 (dd, J=13.8, 6.3 Hz, 1H), 2.54 (dd, J=13.6, 9.4 Hz, 1H), 2.20–2.80 (m, 1H), 1.81 (d, J=5.2 Hz, 1H), 0.74 (s, 9H); $^{13}$C NMR (100 MHz, CDCl$_3$) δ26.64, 30.96, 34.62, 41.53, 64.76, 67.42, 75.33, 116.77, 121.07, 122.97, 124.13, 126.44, 127.50, 127.54, 128.45, 128.60, 128.92, 129.11, 130.25, 130.31, 139.08, 141.69, 142.03, 154.44, 168.14.

EXAMPLE 13

(3S,4R)-2-(3-Benzyl-4-hydroxy-chroman-7-yl)-4-trifluoromethyl-benzoic Acid

A solution of (3S,4R)-2-(3-benzyl-4-hydroxy-chroman-7-yl)-4-trifluoromethyl-benzoic acid 2,2-dimethyl-propyl ester (2.34 g, 4.69 mmol) in isopropyl alcohol (23 mL) was treated with 10% aqueous sodium hydroxide (2.3 mL, 6.4 mmol) and heated at reflux for 3 hours. The reaction mixture was cooled to ambient temperature, poured into water (34 mL), and extracted with hexanes (23 mL) and isopropyl ether (13 mL). The aqueous layer was separated and extracted with hexanes (23 mL) and isopropyl ether (13 mL), adjusted to pH 2 with 6N aqueous hydrochloric acid, and extracted with ethyl acetate (two times 40 mL). The combined ethyl acetate extracts were washed with brine (40 mL), dried over magnesium sulfate, filtered and concentrated to a white foam which was recrystallized from toluene/hexanes. The resulting solids were filtered and washed with hexanes, and the wet cake was stirred with hexanes (20 mL) for 1 hour. The mixture was filtered, and the resulting solids were dried under vacuum to provide 1.01 g (50% yield) of (3S,4R)-2-(3-benzyl-4-hydroxy-chroman-7-yl)-4-trifluoromethyl-benzoic acid as a white solid: $^1$H NMR (400 MHz, CDCl$_3$) δ8.00 (d, J=8.1 Hz, 1H), 7.67 (d, J=8.1 Hz, 1H), 7.64 (s, 1H), 7.18–7.36 (m, 6H), 6.91 (dd, J=7.9, 1H), 6.86 (d, J=1.7 Hz, 1H), 4.53 (d, J=4.2 Hz, 1H), 4.24 (dd, J=11.2, 2.7 Hz, 1H), 3.97 (dd, J=11.0, 4.0 HZ, 1H), 2.76 (dd, J=13.9, 6.4 Hz, 1H), 2.53 (dd, J=13.7, 9.3 Hz, 1H), 2.24–2.26 (m, 1H).

EXAMPLE 14

2-[1,3,6,2]Dioxazaborocan-2-yl-4-trifluoromethyl-benzoic acid 2,2-dimethyl-propyl Ester To a solution of 4-trifluoromethyl-benzoic acid 2,2-dimethyl-propyl ester (35.8 g, 138 mmol) in tetrahydrofuran (250 mL) was added triisopropylborate (73.0 mL, 316 mmol). The solution was cooled to 0° C., lithium diisopropylamide (73.0 mL of a 2.0 M solution in tetrahydrofuran/heptane, 146.0 mmol) was added dropwise over 20 minutes, and the red solution was stirred for an additional 30 minutes. Hexanes (200 mL) was added followed by 1N hydrochloric acid (200 mL). The mixture was stirred for 10 minutes and poured into hexanes (200 mL). The organic layer was washed with 1 N hydrochloric acid (two times 150 mL), and brine (100 mL). The organic extracts were dried over magnesium sulfate, filtered, and concentrated to about 200 mL. Isopropyl alcohol (100 mL), and diethanolamine (15.95 g, 151.7 mmol) were added, and the mixture was stirred at room temperature for 10 hours. The solids were filtered and washed with a mixture of isopropyl alcohol (15 mL) and hexanes (30 mL) to provide 2-[1,3,6,2]dioxazaborocan-2-yl-4-trifluoromethyl-benzoic acid 2,2-dimethyl-propyl ester (37.83 g, 74% yield) as a white solid. mp=233–234° C.; IR 3077, 2963, 2862, 1722, 1480, 1467, 1371, 1331, 1298, 1290, 1279, 1254, 1161, 1117, 1108, 1087, 1074, 995, 952, 862, cm$^{-1}$; $^1$H NMR (400 MHz, CDCl$_3$) d 8.23(s, 1H), 7.72 (d, J=7.9 Hz, 1H), 7.52 (dd, J=7.9, 1.3 Hz, 1H), 6.33 (brs, 1H), 4.08–4.14 (m, 2H), 3.98 (s, 2H), 3.93–3.98 (m, 2H), 3.42–3.50(m, 2H), 2.88–2.94(m, 2H), 1.02 (s, 9H); $^{13}$C NMR (100 MHz, CDCl$_3$) 26.51, 31.69, 50.92, 63.33, 74.72, 123.94, 128.59, 132.06, 139.61, 171.56.

EXAMPLE 15

(3S,4R)-Dicyclohexylammonium-2-(3-benzyl-4-hydroxy-chroman-7-yl)-4-trifluoromethyl-benzoate A mixture of 2-[1,3,6,2]dioxazaborocan-2-yl-4-trifluoromethyl-benzoic acid 2,2-dimethyl-propyl ester (7.04 g, 18.9 mmol) in toluene (45 mL) and 1.5 N hydrochloric acid (45 mL) was stirred at room temperature for 45 minutes. The aqueous layer was removed and sodium carbonate (2.73 g, 25.8 mmol), (3S,4R)-3-benzyl-7-bromo-chroman-4-ol (5.47 g, 17.1 mmol), tetrakis(triphenylphosphine)palladium(0) (24.0 mg, 20.8, μmol), and water (20 mL) were added. The bi-phasic solution was stirred at reflux for 100 minutes, cooled to room temperature, and poured into water (50 mL). The layers were separated, and the organic layer was treated with Darco®G-60, filtered, and concentrated. The crude ester was dissolved in isopropyl alcohol (80 mL) and 10% aqueous sodium hydroxide (8.0 mL) was added. The solution was heated at reflux for 3 hours, cooled to room temperature, poured into water (120 mL), and extracted with hexanes (80 mL) and isopropyl ether (40 mL). The aqueous layer was washed with hexanes (80 mL) and isopropyl ether (40 mL), adjusted to pH 2 with 6 N hydrochloric acid, and extracted with methyl tert-butyl ether (two times 75 mL). The organic extracts were dried over magnesium sulfate, filtered, and concentrated. The crude product was dissolved in methyl tert-butyl ether (40 mL), and dicyclohexylamine (4.10 mL, 20.6 mmol) was added. The mixture as stirred overnight, and the solid was filtered and washed with methyl tert-butyl ether (20 mL) to afford (3S,4R)-dicyclohexylammonium-2-(3-benzyl-4-hydroxy-chroman-7-yl)-4-trifluoromethyl-benzoate (7.32 g, 70% yield): mp=209–210° C.; IR 3307, 3025, 2939, 2858, 1626, 1564, 1429, 1398, 1388, 1333, 1168, 1119, 903, 875, 846, 838 cm$^{-1}$; $^1$H NMR (400 MHz, CDCl$_3$) δ7.62 (d, J=7.7 Hz, 1H), 7.55 (s, 1H), 7.52 (d, J=7.9 Hz, 1H), 7.17–7.31 (m, 6H), 7.08 (dd, J=7.9, 1.7 Hz,1H), 7.00 (d, J=1.7 Hz, 1H), 4.48 (d, J–4.4 Hz, 1H), 4.17 (dd, J=11.0, 2.6 Hz, 1H), 3.90 (dd, J=11.0, 5.0 Hz, 1H), 2.74–2.79 (m, 3H), 2.50 (dd, J=13.8, 9.4 Hz, 1H), 1.80–1.82 (m, 4H), 2.20 (brs, 1H), 1.68–1.70 (m, 4H), 1.56 (d, J=12.2 Hz, 2H), 1.00–1.26 (m, 10H), $^{13}$C NMR (100 MHz, CDCl$_3$) δ24.70, 24.73, 25.03, 28.94, 29.09, 34.75, 41.75, 52.64, 65.00, 67.57, 116.50, 121.42, 122.59, 123.77, 126.38, 126.73, 128.03, 128.55, 129.06, 129.45, 138.95, 139.16, 142.51, 144.20, 154.04, 173.85.

EXAMPLE 16

(3S,4R)-2-(3-Benzyl-4-hydroxy-chroman-7-yl)-4-trifluoromethyl-benzoic Acid

A mixture of (3S,4R)-dicyclohexylammonium-2-(3-benzyl-4-hydroxy-chroman-7-yl)-4-trifluoromethyl-benzoate (2.37 g, 3.89 mmol) in ethyl acetate (25 mL), and 1 N hydrochloric acid (25 mL) was stirred at room temperature for 1 hour. The mixture was poured into ethyl acetate (20 mL) and the aqueous layer was removed. The organic layer was washed with water (six times 50 mL), dried over magnesium sulfate, filtered, and concentrated to provide (3 S,4 R)-2-(3-benzyl-4-hydroxy-chroman-7-yl)-4-trifluoromethyl-benzoic acid (1.66 g, 100% yield): $^1$H NMR (400 MHz, CDCl$_3$) δ8.00 (d, J=8.1 Hz, 1H), 7.67 (d, J=8.1 Hz, 1H), 7.64 (s, 1H), 7.18–7.36 (m, 6H), (dd, J=7.9,1.7 Hz, 1H), 6.86 (d, J=1.7 Hz, 1H), 4.53 (d, J=4.2 Hz, 1H), 4.2 (dd, J=11.2, 2.7 Hz, 1H), 3.97 (dd, J=11.0, 4.0 Hz, 1H), 2.76 (dd, J=13.9, 6.4 Hz, 1H), 2.53 (dd, J=13.7,9.3 Hz, 1H), 2.24–2.26 (m, 1H).

EXAMPLE 17

[[3(2R,3R)]-4R,5S]-3-[2-Benzyl-3-(4-bromo-2-fluoro-phenyl)-3-hydroxy-propionyl]-4-methyl-5-phenyl-oxazolidin-2-one To a solution of (4R,5S)-4-methyl-5-phenyl-3-(3-phenyl-propionyl)-oxazolidin-2-one (1.50 g, 4.8 mmol) in dichloromethane (23 mL) at −70° C. was added titanium tetrachloride (0.6 mL, 5.3 mmol) giving a yellow-orange solution which was stirred for 15 minutes at −70° C. N,N,N',N'-Tetramethylethylenediamine(2.2 mL, 15 mmol) was added over 10 minutes giving a dark red reaction mixture which was stirred for 70 minutes at −78° C. 1-Methyl-2-pyrrolidinone (0.90 mL, 9.7 mmol) was added dropwise, and the reaction mixture was stirred for 30 minutes at −70° C. A solution of 4-bromo-2-fluoro-benzaldehyde (0.990 g, 4.9 mmol) in dichloromethane (5 mL) was added dropwise while maintaining a reaction temperature of less than or equal to −68° C. The reaction mixture was stirred at −70° C. for 60 minutes and then allowed to warm to 0° C. over 90 minutes, at which point it was quenched with 15 mL of saturated aqueous ammonium chloride and 1.2 g. of Celite®. This mixture was stirred overnight at room temperature and filtered. The phases were separated and the organic phase was washed three times with water and once with brine, dried over magnesium sulfate, and concentrated under vacuum to 2.76 g of an oil containing the title compound and 1.2 equivalents of 1-methyl-2-pyrrolidinone: $^1$H NMR (400 MHz, CDCl$_3$) δ7.48 (t, J=8.1 Hz, 1H), 7.09–7.34 (m, 12H), 5.35 (d, J=7.3 Hz, 1H), 5.32 (d, J=4.9 Hz, 1H), 4.89–4.92 (m, 1H), 4.51–4.55 (m, 1H), 3.65 (bs, 1H), 3.35 (dd, J=7.1, 7.1 Hz, 2H), 3.03–3.06 (m,2H), 2.81 (s, 3H), 2.34 (dd, J=8.1, 8.1 Hz, 2H), 1.95–2.03 (m, 2H), 0.40 (d, J=6.6 Hz, 3H).

What is claimed is:

1. A compound of the formula

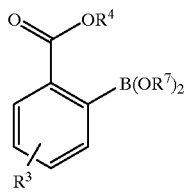

XIII wherein R$^3$ is selected from the group consisting of H, fluoro, chloro, C$_1$–C$_6$ alkyl, C$_1$–C$_6$ alkoxy, phenylsulfinyl, phenylsulfonyl, and —S(O)$_n$(C$_1$–C$_6$ alkyl) wherein n is 0 to 2, and wherein said alkyl group, the alkyl moiety of said alkoxy and —S(O)$_n$(C$_1$–C$_6$ alkyl) groups, and the phenyl moiety of said phenylsulfinyl and phenylsulfonyl groups are optionally substituted by 1 to 3 fluoro groups;

R$^4$ is C$_1$–C$_6$ alkyl; and,

R$^7$ is C$_1$–C$_6$ alkyl.

2. A compound of the formula

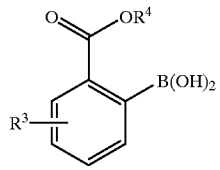

XIV wherein R$^3$ is selected from the group consisting of H, fluoro, chloro, C$_1$–C$_6$ alkyl, C$_1$–C$_6$ alkoxy, phenylsulfinyl, phenylsulfonyl, and —S(O)$_n$(C$_1$–C$_6$ alkyl) wherein n is 0 to 2, and wherein said alkyl group, the alkyl moiety of said alkoxy and —S(O)$_n$(C$_1$–C$_6$ alkyl) groups, and the phenyl moiety of said phenylsulfinyl and phenylsulfonyl groups are optionally substituted by 1 to 3 fluoro groups; and, R$^4$ is C$_1$–C$_6$ alkyl.

3. A compound of the formula

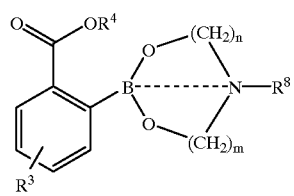

XVI wherein the dashed line indicates a bond or no bond between the B and N atoms;

n and m are independently 2 to 5;

R$^3$ is selected from the group consisting of H, fluoro, chloro, C$_1$–C$_6$ alkyl, C$_1$–C$_6$ alkoxy, phenylsulfinyl, phenylsulfonyl, and —S(O)$_n$(C$_1$–C$_6$ alkyl) wherein n is 0 to 2, and wherein said alkyl group, the alkyl moiety of said alkoxy and —S(O)$_n$(C$_1$–C$_6$ alkyl) groups, and the phenyl moiety of said phenylsulfinyl and phenylsulfonyl groups are optionally substituted by 1 to 3 fluoro groups;

R$^4$ is C$_1$–C$_6$ alkyl; and,

R$^8$ is H or C$_1$–C$_6$ alkyl.

* * * * *